United States Patent
Fujiyama et al.

(10) Patent No.: US 8,294,144 B2
(45) Date of Patent: Oct. 23, 2012

(54) ORGANIC TRANSISTOR

(75) Inventors: Takahiro Fujiyama, Sodegaura (JP);
Yoshiyuki Totani, Sodegaura (JP);
Masakatsu Nakatsuka, Sodegaura (JP)

(73) Assignee: Yamamoto Chemicals, Inc., Yao-shi, Osaka (JP)

( * ) Notice: Subject to any disclaimer, the term of this patent is extended or adjusted under 35 U.S.C. 154(b) by 230 days.

(21) Appl. No.: 12/921,757

(22) PCT Filed: Sep. 12, 2008

(86) PCT No.: PCT/JP2008/066544
§ 371 (c)(1), (2), (4) Date: Sep. 9, 2010

(87) PCT Pub. No.: WO2009/113194
PCT Pub. Date: Sep. 17, 2009

(65) Prior Publication Data
US 2011/0012098 A1    Jan. 20, 2011

(30) Foreign Application Priority Data
Mar. 10, 2008 (JP) ................................ 2008-059378

(51) Int. Cl.
*H01L 35/24* (2006.01)
(52) U.S. Cl. .................................. 257/40; 257/E51.001
(58) Field of Classification Search .................... 257/40, 257/E51.001
See application file for complete search history.

(56) References Cited

U.S. PATENT DOCUMENTS
6,291,621 B1    9/2001  Tan

FOREIGN PATENT DOCUMENTS
JP    2005-519486 A    6/2005
JP    2005-347661 A    12/2005
(Continued)

OTHER PUBLICATIONS
H. Fuchigami, et al., Polythienylenevinylene thin-film transistor with high carrier mobility, Appl. Phys. Lett. vol. 63, No. 10, Sep. 6, 1993, pp. 1372-1374.

(Continued)

*Primary Examiner* — Anthony Ho
(74) *Attorney, Agent, or Firm* — Knobbe Martens Olson & Bear LLP

(57) ABSTRACT

In order to attain high mobility, large on/off current ratio and excellent storage stability to organic transistor comprising an organic semiconductor layer, the organic semiconductor layer comprises at least one compound represented by the general formula (1):

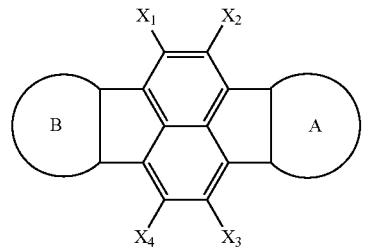

Figure 1:
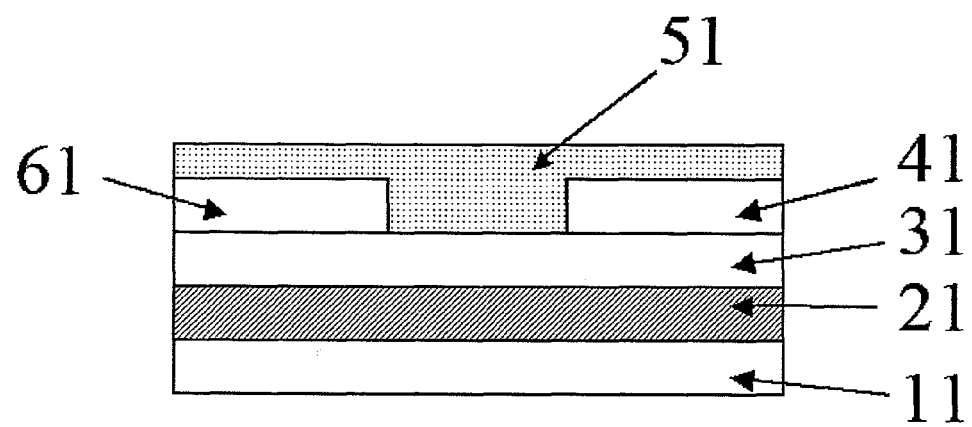

(wherein each of $X_1$ to $X_4$ represents independently a hydrogen atom, a halogen atom, a straight, branched or cyclic alkyl group, a straight, branched or cyclic alkoxy group, a straight, branched or cyclic alkoxyalkyl group, or an unsubstituted or substituted aryl group, A represents an unsubstituted or substituted thiophene ring, B represents an unsubstituted or substituted benzene ring, or an unsubstituted or substituted thiophene ring).

2 Claims, 2 Drawing Sheets

FOREIGN PATENT DOCUMENTS

| JP | 2005347661 | 12/2005 |
|----|------------|---------|
| JP | 2007-99736 A | 4/2007 |
| WO | WO 03/077327 A1 | 9/2003 |

OTHER PUBLICATIONS

A. Dodabalapur, et al., Organic Transistors: Two-Dimensional Transport and Improved Electrical Characteristics, Science vol. 268, Apr. 14, 1995, pp. 270-271.

Norio Miyaura, et al., Palladium-Catalyzed Cross-Coupling Reactions of Organoboron Compounds, 1995 American Chemical Society, Chemical Reviews, 1995, vol. 95, No. 7, pp. 2457-2483, Revised Manuscript.

S.F. Nelson, et al., Temperature-independent transport in high-mobility pentacene transistors, 1998 American Institute of Physics, Applied Physics Letters, vol. 72, No. 15, 13 April 2998, pp. 1854-1856.

Dino Alberico, et al., Ary-Aryl Bond Formation by Transition-Metal-Catalyzed Direct Arylation, 2007 American Chemical Society, Chemical Reviews, 2007 vol. 107, No. 1, Published on Web 01/10/1007 pp. 174-238.

European Search Report; Apr. 14, 2011; Application No. 08873339.9; PCT/JP2008/066544.

ORGANIC TRANSISTOR

FIELD OF THE INVENTION

This invention relates to an organic transistor. More particularly, it relates to an organic transistor using a specific organic compound in an organic semiconductor layer.

RELATED ART

Conventionally, a thin film transistor (TFT), which is formed using amorphous silicon or polycrystalline silicon, has been widely used as a switching element for a flat panel display such as liquid crystal device. However, there are problems that CVD equipments used for preparing thin film transistors using such silicon is expensive, and the preparation of large thin film transistor device leads to an increase in manufacturing cost.

Also, since the formation of films from amorphous silicon or polycrystalline silicon is performed at high temperature, there is a problem that materials such as plastics, which have a lightweight and flexibility but lack thermal resistance, cannot be used as a substrate.

In order to solve the above problems, an organic transistor (organic thin film transistor, also it is referred to as "organic TFT") in which an organic compound is used in a channel semiconductor layer (hereinafter, it is referred to as "organic semiconductor layer"), instead of amorphous silicon or polycrystalline silicon, had been proposed (non-patent document 1).

As a method for forming an organic semiconductor layer, for example, vacuum vapor deposition or coating methods and the like have been known, and these methods allow the inhibition of manufacturing cost while facilitating size-up of organic transistor devices.

Furthermore, since a temperature that is required to form films can be reduced, it is possible to use plastic materials in a substrate and apply to flexible display elements, thereby raising the expectation on practical use of such techniques.

A practicable organic transistor needs to have properties such as high charge mobility and high current on/off ratio. The term "on/off ratio" as used herein means a ratio of the current between a source electrode and a drain electrode when an organic transistor is on to the current between the source electrode and the drain electrode when the organic transistor is off.

In addition, excellent storage stability is required to put an organic transistor to practical use.

To date, an organic transistor in which, e.g., pentacene is used in an organic semiconductor layer had been proposed (non-patent document 2).

However, the organic transistor using pentacene has the problem that it has low organic transistor functionality as well as low storage stability in air.

Also, an organic transistor in which thiophene oligomer (α-hexathienylene) is used in an organic semiconductor layer had been proposed (non-patent document 3). However, said organic transistor has also the problem that it has low storage stability in air.

Furthermore, it was described that dibenzo[a,j]naphthacene or dibenzo[de,qr] naphthacene is useful in an organic semiconductor layer of organic transistors (patent document 1). However, it was found that organic transistors using such dibenzo-naphthacenes in an organic semiconductor layer have also the problem of low charge mobility.

Currently, there is a demand for the development of a more improved organic transistor for practical use.

Non-patent document 1: Appl. Phys. Lett., 63, 1372 (1993)
Non-patent document 2: Appl. Phys. Lett., 72, 1854 (1998)
Non-patent document 3: Science, 268, 270 (1995)
Patent document 1: JP 2005-519486A

SUMMARY

To date, organic transistors in which various organic compounds are used in an organic semiconductor layer have been proposed, but it was difficult to say that all of these transistors have properties enough to meet practicality.

With the aforementioned matters in mind, the present invention is to provide an organic transistor having high charge mobility, high current on/off ratio, and excellent storage stability.

As the result of studying zealously to solve the above-mentioned problems, the inventors discovered the fact that an organic transistor which is formed by containing a compound represented by the general formula (1) in an organic semiconductor layer has high charge mobility, high current on/off ratio, and excellent storage stability, and the present invention has been completed on the basis of such finding.

That is, the present invention is an organic transistor comprising an organic semiconductor layer wherein the organic transistor is formed by containing at least one compound represented by the following general formula (1) in the organic semiconductor layer.

[C1]

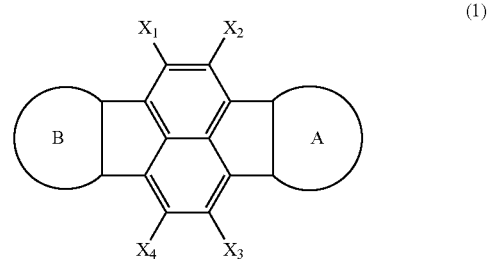

(1)

(wherein each of $X_1$ to $X_4$ represents independently a hydrogen atom, a halogen atom, a straight, branched or cyclic alkyl group, a straight, branched or cyclic alkoxy group, a straight, branched or cyclic alkoxyalkyl group, or an unsubstituted or substituted aryl group, A represents an unsubstituted or substituted thiophene ring, B represents an unsubstituted or substituted benzene ring, or an unsubstituted or substituted thiophene ring)

According to the present invention, it is possible to provide an organic transistor having high charge mobility, a high current on/off ratio, and excellent storage stability.

BRIEF DESCRIPTIONS OF THE DRAWINGS

Figure 2:
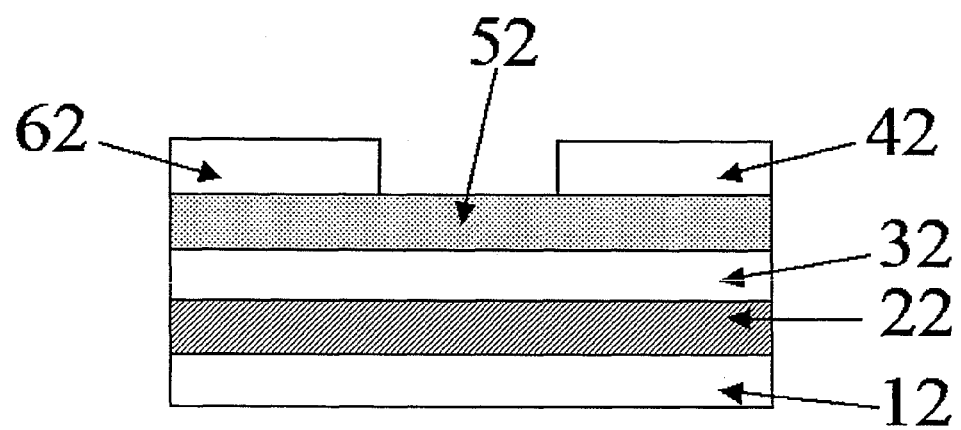
Figure 3:
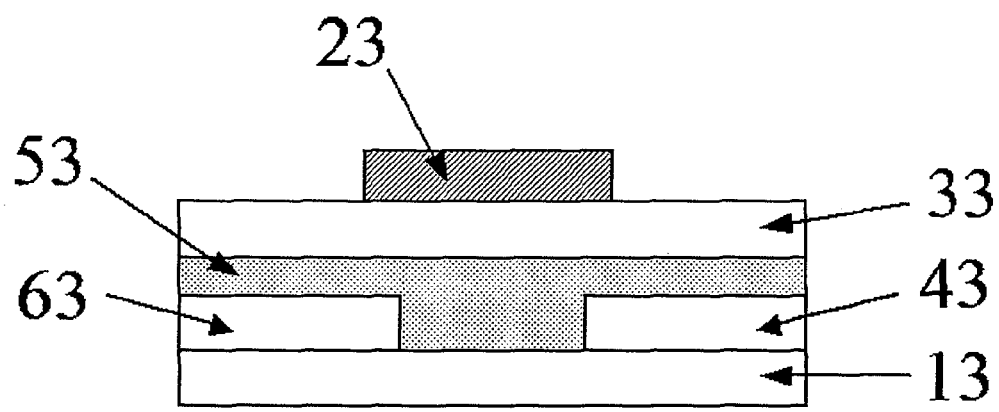
Figure 4:
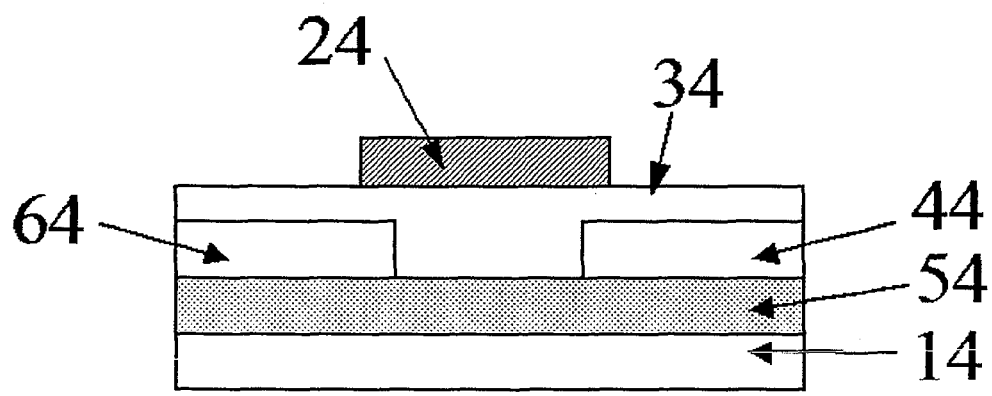

FIG. 1 shows a schematic cross-sectional view of an organic transistor according to this invention.
FIG. 2 shows a schematic cross-sectional view of an organic transistor according to this invention.
FIG. 3 shows a schematic cross-sectional view of an organic transistor according to this invention.
FIG. 4 shows a schematic cross-sectional view of an organic transistor according to this invention.

DESCRIPTIONS OF REFERENCE NUMERALS

11: substrate
21: gate electrode

31: gate insulating layer
41: drain electrode
51: organic semiconductor layer
61: source electrode
12: substrate
22: gate electrode
32: gate insulating layer
42: drain electrode
52: organic semiconductor layer
62: source electrode
13: substrate
23: gate electrode
33: gate insulating layer
43: drain electrode
53: organic semiconductor layer
63: source electrode
14: substrate
24: gate electrode
34: gate insulating layer
44: drain electrode
54: organic semiconductor layer
64: source electrode

DETAILED DESCRIPTION OF THE PREFERRED EMBODIMENTS

In the following, this invention will be described in detail.

An organic transistor according to this invention is formed by containing at least one compound represented by the following general formula (1) in an organic semiconductor layer.

[C2]

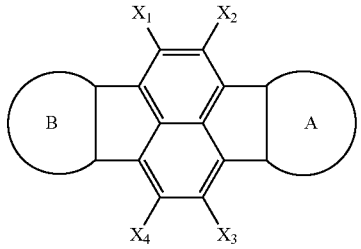

(1)

(wherein each of $X_1$ to $X_4$ represents independently a hydrogen atom, a halogen atom, a straight, branched or cyclic alkyl group, a straight, branched or cyclic alkoxy group, a straight, branched or cyclic alkoxyalkyl group, or an unsubstituted or substituted aryl group, A represents an unsubstituted or substituted thiophene ring, B represents an unsubstituted or substituted benzene ring, or an unsubstituted or substituted thiophene ring)

In the compound represented by the general formula (1), each $X_1$ to $X_4$ represents independently a hydrogen atom, a halogen atom, a straight, branched or cyclic alkyl group, a straight, branched or cyclic alkoxy group, a straight, branched or cyclic alkoxy alkyl group, or an unsubstituted or substituted aryl group. Meanwhile, in the present disclosure, aryl groups represent carbocyclic aromatic groups such as phenyl, naphthyl group and the like; heterocyclic aromatic groups such as furyl, thienyl, pyridyl group and the like. Also, substituents on such aryl groups include a halogen atom, a straight, branched or cyclic alkyl group having 1 to 20 carbon atoms, a straight, branched or cyclic alkoxy group having 1 to 20 carbon atoms, or an aryl group having 4 to 20 carbon atoms which may substituted by said halogen atom, alkyl group, alkoxy group.

In the compound represented by the general formula (1), more preferably, $X_1$ to $X_4$ represent a hydrogen atom, a halogen atom, a straight, branched or cyclic alkyl group having 1 to 20 carbon atoms, a straight, branched or cyclic alkoxy group having 1 to 20 carbon atoms, a straight, branched or cyclic alkoxyalkyl group having 2 to 20 carbon atoms, or an unsubstituted or substituted aryl group having 4 to 20 carbon atoms.

In the general formula (1), specific examples of $X_1$ to $X_4$ include, for example, a hydrogen atom; halogen atoms such as fluorine, chlorine, bromine atom and the like; straight, branched or cyclic alkyl groups such as methyl, ethyl, n-propyl, isopropyl, n-butyl, isobutyl, sec-butyl, tert-butyl, n-pentyl, isopentyl, neopentyl, tert-pentyl, n-hexyl, 1-methylpentyl, 4-methyl-2-pentyl, 3,3-dimethylbutyl, 2-ethylbutyl, n-heptyl, 1-methyl-hexyl, cyclohexylmethyl, n-octyl, tert-octyl, 1-methylheptyl, 2-ethylhexyl, 2-propyl-pentyl, n-nonyl, 2,2-dimethylheptyl, 2,6-dimethyl-4-heptyl, 3,5,5-trimethylhexyl, n-decyl, n-undecyl, 1-methyldecyl, n-dodecyl, n-tridecyl, 1-hexylheptyl, n-tetradecyl, n-pentadecyl, n-hexadecyl, n-heptadecyl, n-octadecyl, n-eicosyl, cyclopentyl, cyclohexyl, 4-methylcyclohexyl, 4-tert-butylcyclohexyl, cycloheptyl, cyclooctyl group and the like;

straight, branched or cyclic alkoxy groups such as methoxy, ethoxy, n-propoxy, isopropoxy, n-butoxy, isobutoxy, sec-butoxy, n-pentyloxy, neopentyloxy, cyclopentyloxy, n-hexyloxy, 3,3-dimethylbutyloxy, 2-ethylbutyloxy, cyclohexyloxy, n-heptyloxy, n-octyloxy, 2-ethylhexyloxy, n-nonyloxy, n-decyloxy, n-undecyloxy, n-dodecyloxy, n-tridecyloxy, n-tetradecyloxy, n-pentadecyloxy, n-hexadecyloxy, n-heptadecyloxy, n-octadecyloxy, n-eicosyloxy group and the like;

straight, branched or cyclic alkoxyalkyl groups such as methoxymethyl, ethoxy-methyl, n-butoxymethyl, n-hexyloxymethyl, (2-ethylbutyloxy)methyl, n-octyloxy-methyl, n-decyloxymethyl, 2-methoxyethyl, 2-ethoxyethyl, 2-n-propoxyethyl, 2-isopropoxyethyl, 2-n-butoxyethyl, 2-n-pentyloxyethyl, 2-n-hexyloxyethyl, 2-(2'-ethylbutyloxy)ethyl, 2-n-heptyloxyethyl, 2-n-octyloxyethyl, 2-(2'-ethyl hexyloxy)ethyl, 2-n-decyloxyethyl, 2-n-dodecyloxyethyl, 2-n-tetradecyloxyethyl, 2-cyclohexyloxyethyl, 2-methoxypropyl, 3-methoxypropyl, 3-ethoxypropyl, 3-n-propoxypropyl, 3-isopropoxy-propyl, 3-n-butoxypropyl, 3-n-pentyloxypropyl, 3-n-hexyloxypropyl, 3-(2'-ethyl-butoxy)propyl, 3-n-octyloxypropyl, 3-(2'-ethylhexyloxy)propyl, 3-n-decyloxypropyl, 3-n-dodecyloxypropyl, 3-n-tetradecyloxypropyl, 3-cyclohexyloxypropyl, 4-methoxybutyl, 4-ethoxybutyl, 4-n-propoxybutyl, 4-isopropoxybutyl, 4-n-butoxybutyl, 4-n-hexyl-oxybutyl, 4-n-octyloxybutyl, 4-n-decyloxybutyl, 4-n-dodecyloxybutyl, 5-methoxypentyl, 5-ethoxypentyl, 5-n-propoxypentyl, 5-n-pentyloxypentyl, 6-methoxyhexyl, 6-ethoxy-hexyl, 6-isopropoxyhexyl, 6-n-butoxyhexyl, 6-n-hexyloxyhexyl, 6-n-decyloxyhexyl, 4-methoxycyclohexyl, 7-methoxyheptyl, 7-ethoxyheptyl, 7-isopropoxyheptyl, 8-methoxy-octyl, 8-ethoxyoctyl, 9-methoxynonyl, 9-ethoxynonyl, 10-methoxydecyl, 10-ethoxy-decyl, 10-n-butoxydecyl, 11-methoxyundecyl, 11-ethoxyundecyl, 12-methoxydodecyl, 12-ethoxydodecyl, 12-isopropoxydodecyl, 14-methoxytetradecyl, tetrahydrofurfuryl group and the like;

unsubstituted or substituted aryl groups such as phenyl, 2-methylphenyl, 3-methylphenyl, 4-methylphenyl, 4-ethylphenyl, 4-n-propylphenyl, 4-isopropylphenyl, 4-n-butylphenyl, 4-isobutylphenyl, 4-tert-butylphenyl, 4-isopentylphenyl, 4-tert-pentyl-phenyl, 4-n-hexylphenyl, 4-cyclohexylphenyl, 4-n-heptylphenyl, 4-n-octylphenyl, 4-n-nonylphenyl, 4-n-decylphenyl, 4-n-undecylphenyl, 4-n-dodecylphenyl, 4-n-tetradecyl-phenyl, 2,3-dimethylphenyl, 2,4-dimethylphenyl, 2,5-dimethylphenyl, 2,6-dimethyl-phenyl, 3,4-dimethylphenyl, 3,5-dimethylphenyl, 3,4,5-trimethylphenyl, 2,3,5,6-tetra-methylphenyl, 5-indanyl, 1,2,3,4-tetrahydro-5-naphthyl, 1,2,3,4-tetrahydro-6-naphthyl, 2-methoxyphenyl, 3-methoxyphenyl, 4-methoxyphenyl, 3-ethoxyphenyl, 4-ethoxy-phenyl, 4-n-propoxyphenyl, 4-isopropoxyphenyl, 4-n-butoxyphenyl, 4-isobutoxyphenyl, 4-n-pentyloxyphenyl, 4-n-hexyloxyphenyl, 4-cyclohexyloxyphenyl, 4-n-heptyloxy-phenyl, 4-n-octyloxyphenyl, 4-n-nonyloxyphenyl, 4-n-decyloxyphenyl, 4-n-undecyl-oxyphenyl, 4-n-dodecyloxyphenyl, 4-n-tetradecyloxyphenyl, 2,3-dimethoxyphenyl, 2,4-dimethoxyphenyl, 2,5-dimethoxyphenyl, 3,4-dimethoxyphenyl, 3,5-dimethoxyphenyl, 3,5-diethoxyphenyl, 2-methoxy-4-methylphenyl, 2-methoxy-5-methylphenyl, 2-methyl-4-methoxyphenyl, 3-methyl-4-methoxyphenyl, 3-methyl-5-methoxyphenyl, 2-fluoro-phenyl, 3-fluorophenyl, 4-fluorophenyl, 2-chlorophenyl, 3-chlorophenyl, 4-chlorophenyl, 4-bromophenyl, 4-trifluoromethylphenyl, 2,4-difluorophenyl, 2,4-dichloro-phenyl, 3,4-dichlorophenyl, 3,5-dichlorophenyl, 2-methyl-4-chlorophenyl, 2-chloro-4-methylphenyl, 3-chloro-4-methylphenyl, 2-chloro-4-methoxyphenyl, 3-methoxy-4-fluorophenyl, 3-methoxy-4-chlorophenyl, 3-fluoro-4-methoxyphenyl, 2,3,4,5,6-pentafluorophenyl, 4-phenylphenyl, 3-phenylphenyl, 4-(4'-methylphenyl)phenyl, 4-(4'-methoxyphenyl)phenyl, 1-naphthyl, 2-naphthyl, 4-methyl-1-naphthyl, 4-ethoxy-1-naphthyl, 6-n-butyl-2-naphthyl, 6-methoxy-2-naphthyl, 7-ethoxy-2-naphthyl, 2-furyl, 2-thienyl, 5-n-propyl-2-thienyl, 5-n-hexyl-2-thienyl, 5-n-decyl-2-thienyl, 5-phenyl-2-thienyl, 5-(2'-thienyl)-2-thienyl, 3-thienyl, 2-pyridyl, 3-pyridyl, 4-pyridyl group and the like.

More preferably, $X_1$ to $X_4$ is a hydrogen atom, a fluorine atom, a chlorine atom, an alkyl group having 1 to 16 carbon atoms, an alkoxy group having 1 to 16 carbon atoms, an alkoxyalkyl group having 2 to 16 carbon atoms, or an aryl group having 6 to 20 carbon atoms.

In the compound represented by the general formula (1), A represents an unsubstituted or substituted thiophene ring, and the thiophene ring may be substituted, for example, by a halogen atom, a straight, branched or cyclic alkyl group, a straight, branched or cyclic alkoxy group, a straight, branched or cyclic alkoxyalkyl group, or an unsubstituted or substituted aryl group. More preferably, A represents a thoiphene ring which may have a substituent of halogen atoms, straight, branched or cyclic alkyl groups having 1 to 20 carbon atoms, straight, branched or cyclic alkoxy groups having 1 to 20 carbon atoms, straight, branched or cyclic alkoxyalkyl groups having 2 to 20 carbon atoms, or unsubstituted or substituted aryl groups having 4 to 20 carbon atoms as exemplified by $X_1$ to $X_4$. The thiophene ring is preferably a thiophene ring that is ring-fused at 2- and 3-positions, or a thiophene ring that is ring-fused at 3- and 4-positions. The compound represented by the general formula (1) is represented by the following general formulas (1-A) or (1-B) depending on the type of ring A.

[C3]

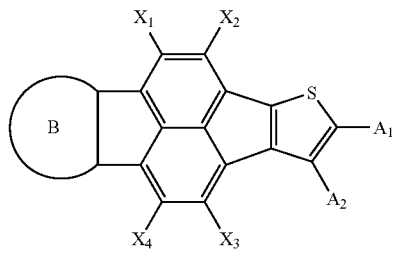

(1-A)

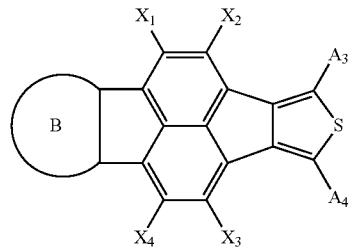

(1-B)

(wherein $X_1$ to $X_4$ and the ring B have the same meanings as defined in the general formula (1), each of $A_1$ to $A_4$ represents independently a hydrogen atom, a halogen atom, a straight, branched or cyclic alkyl group, a straight, branched or cyclic alkoxy group, a straight, branched or cyclic alkoxyalkyl group, or an unsubstituted or substituted aryl group)

In the compound represented by the general formula (1), B represents an unsubstituted or substituted benzene ring, or an unsubstituted or substituted thiophene ring, and both of the benzene and thiophene ring may have a substituent, for example, a halogen atom, a straight, branched or cyclic alkyl group, a straight, branched or cyclic alkoxy group, a straight, branched or cyclic alkoxyalkyl group, or an unsubstituted or substituted aryl group.

More preferably, B represents a benzene ring which may be substituted by halogen atoms, straight, branched or cyclic alkyl groups having 1 to 20 carbon atoms, straight, branched or cyclic alkoxy groups having 1 to 20 carbon atoms, straight, branched or cyclic alkoxyalkyl groups having 2 to 20 carbon atoms, or unsubstituted or substituted aryl groups having 4 to 20 carbon atoms as exemplified by $X_1$ to $X_4$, or a thiophene ring which may be substituted by halogen atoms, straight, branched or cyclic alkyl groups having 1 to 20 carbon atoms, straight, branched or cyclic alkoxy groups having 1 to 20 carbon atoms, straight, branched or cyclic alkoxyalkyl groups having 2 to 20 carbon atoms, or unsubstituted or substituted aryl groups having 4 to 20 carbon atoms as exemplified by $X_1$ to $X_4$.

Herein, the benzene ring is a benzene ring that is ring-fused at an ortho-position, and the thiophene ring is preferably a thiophene ring that is ring-fused at 2- and 3-positions, or a thiophene ring that is ring-fused at 3- and 4-positions.

An organic transistor according to this invention has a characteristic property in that an organic semiconductor layer contains at least one compound represented by the general formula (1), thereby permitting to provide a non-conventional organic transistor having high charge mobility, high current on/off ratio, and excellent storage stability.

With regard to this invention, specific examples of the compounds represented by the general formula (1) include, for example, the following compounds, but this invention should not be limited to these compounds.

Exemplary Compounds
[C4]
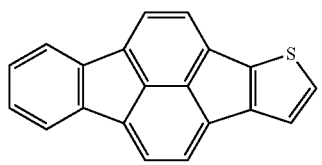
1
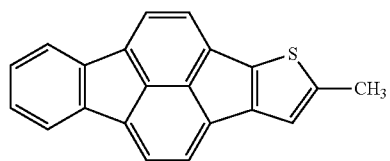
2
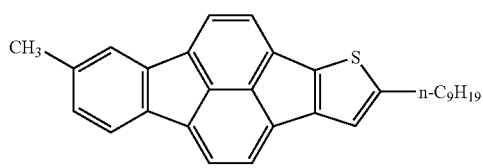
3
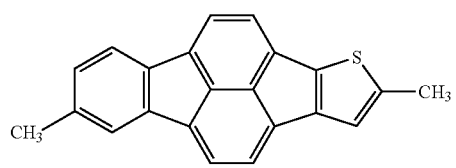
4
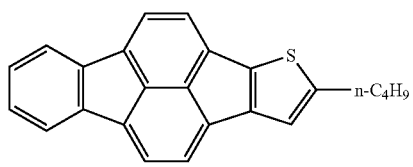
5
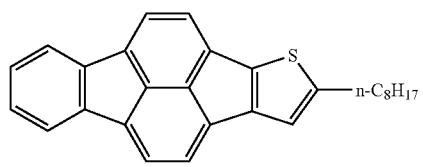
6
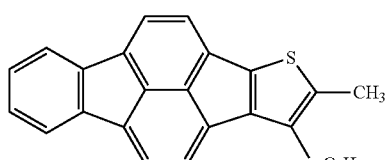
7
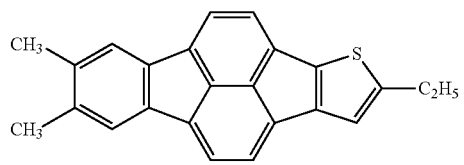
8
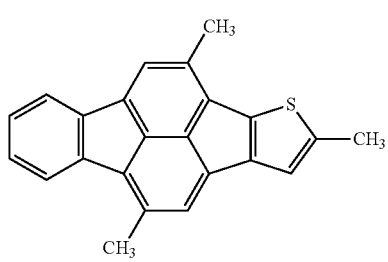
9
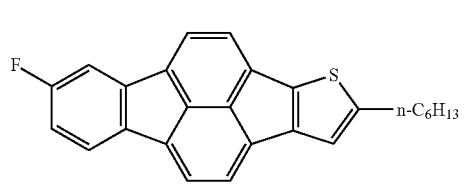
10
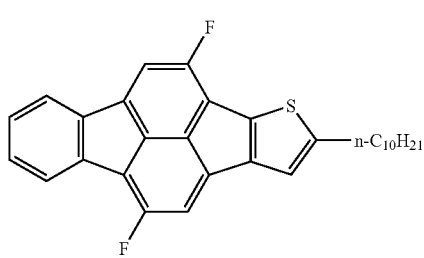
11
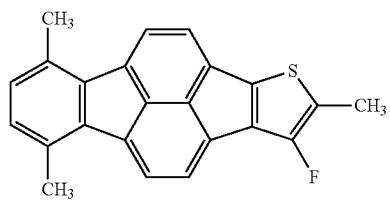
12
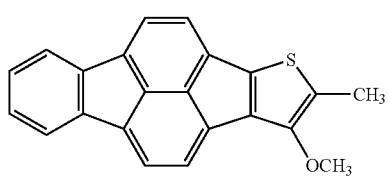
13
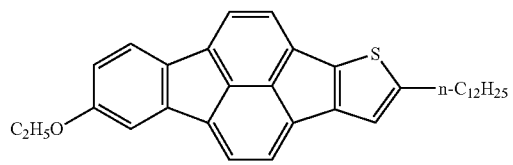
14

-continued
| | | | |
|---|---|---|---|
| 15 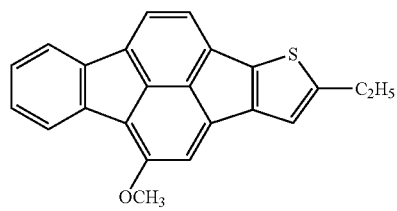 | | 16 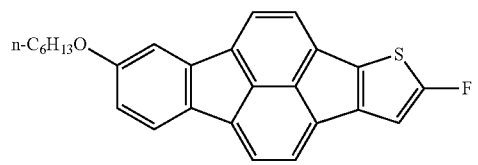 | |
| 17 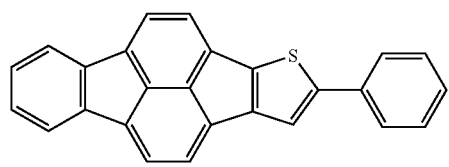 | | 18 | |
| 19 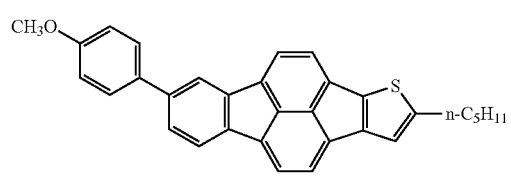 | | 20 | |
| 21 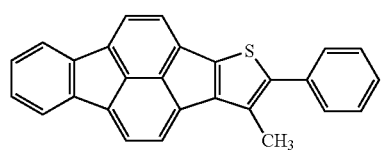 | | 22 | |
| 23 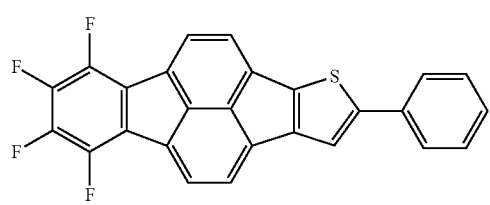 | | 24 | |
| 25 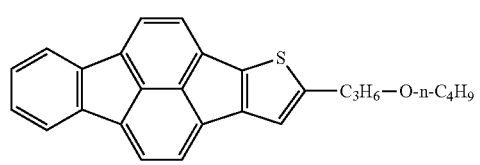 | | 26 | |
| 27 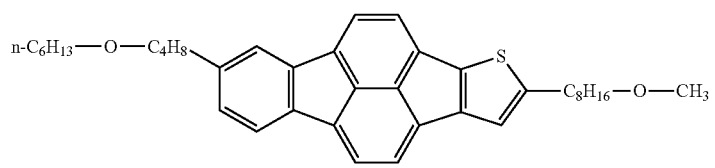 | | | |
| 28 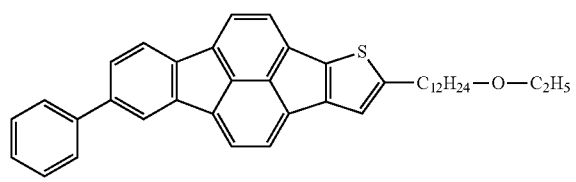 | | 29 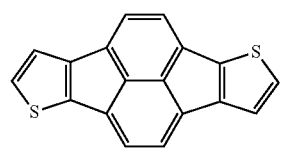 | |

-continued
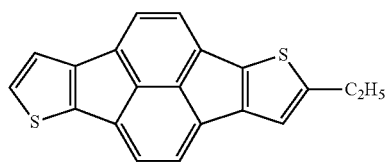
30
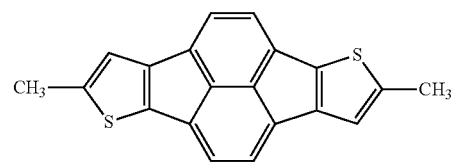
31
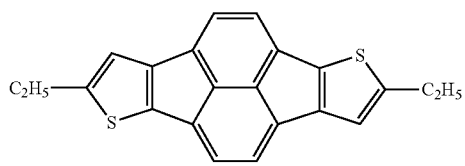
32
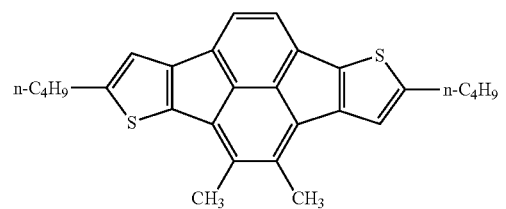
33
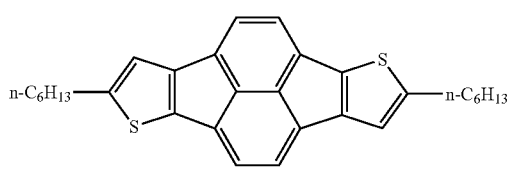
34
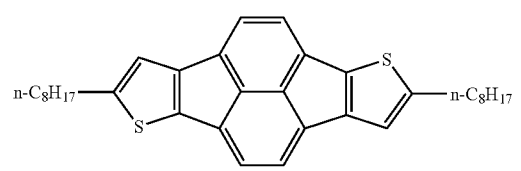
35
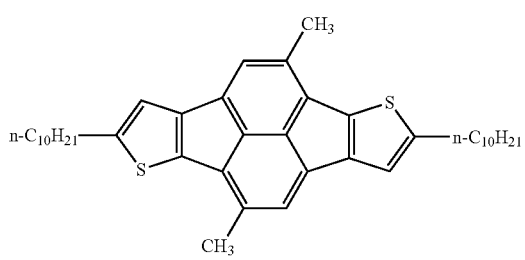
36
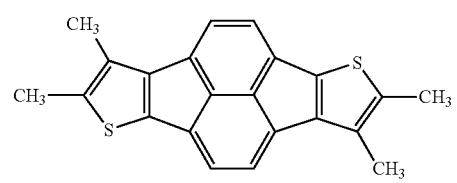
37
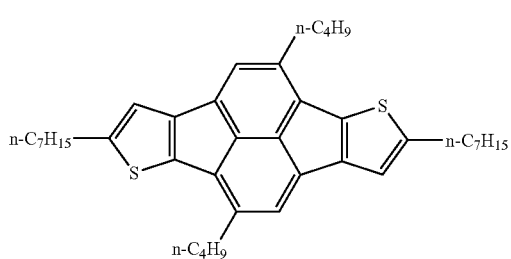
38
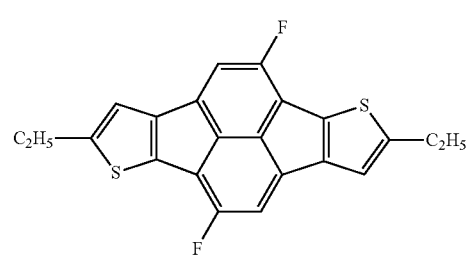
39
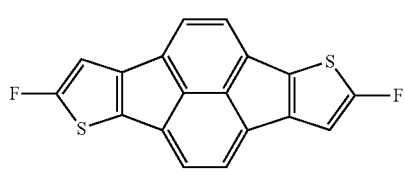
40
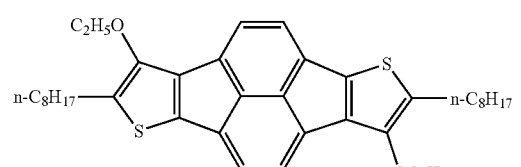
41
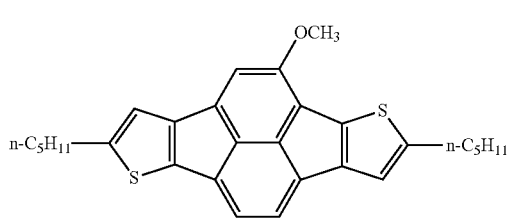
42
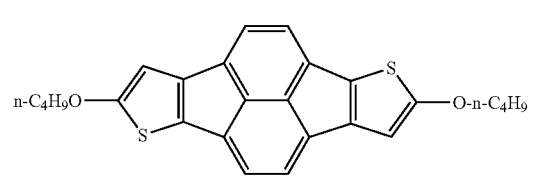
43

-continued
44
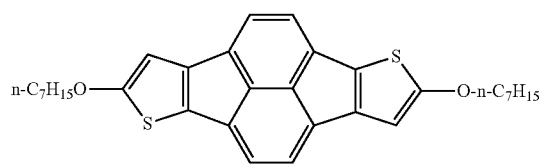
45
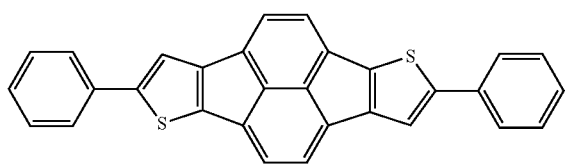
46
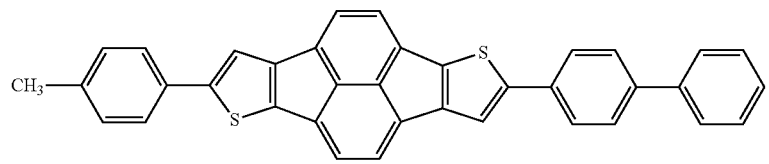
47
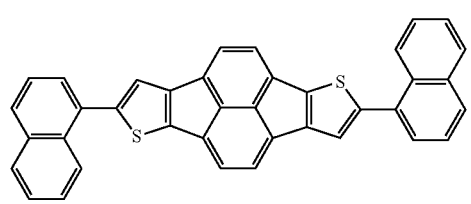
48
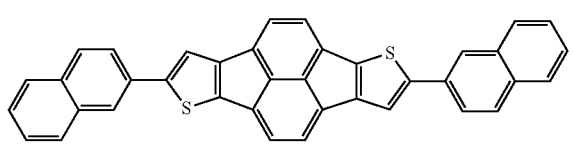
49
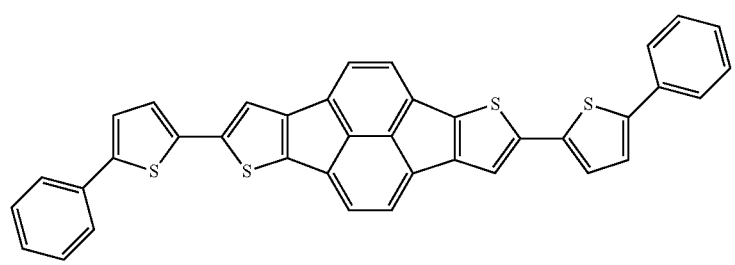
50
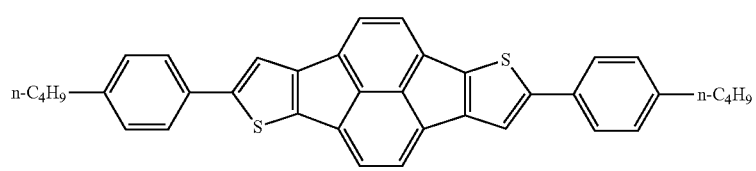
51
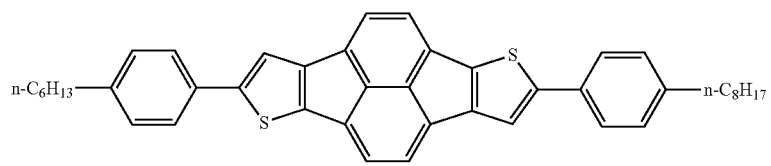
52
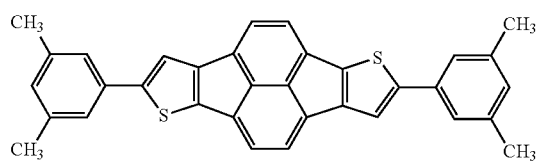
53
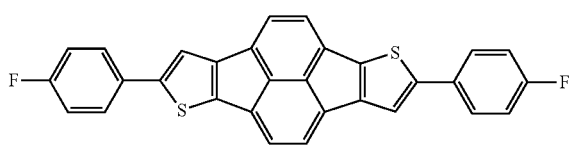
54
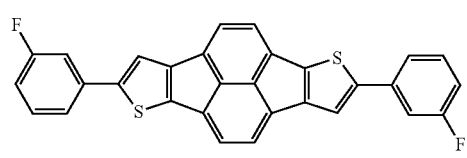
55
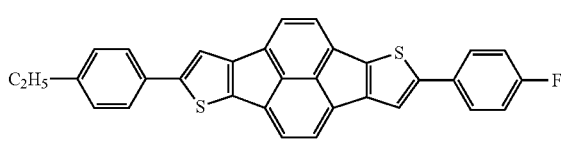

-continued
56
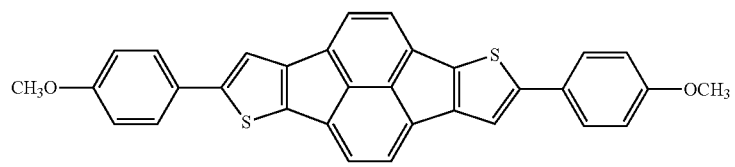
57
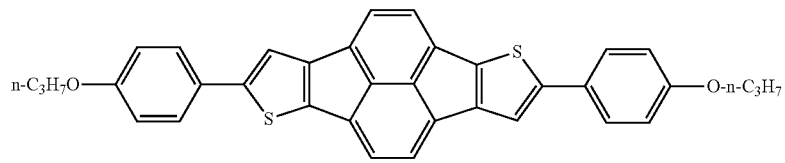
58
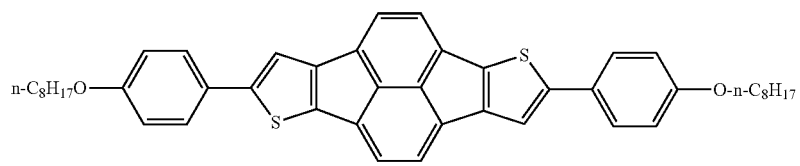
59
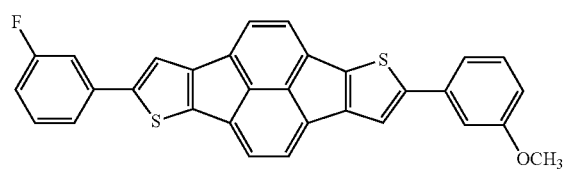
60
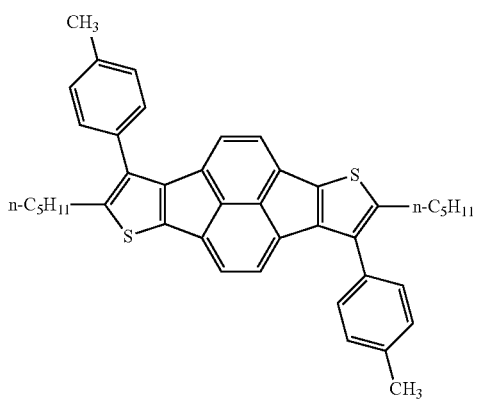
61
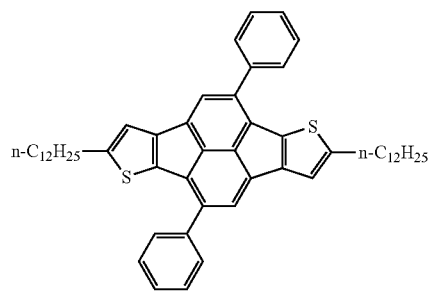
62
63
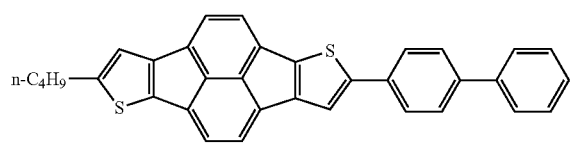
64
65
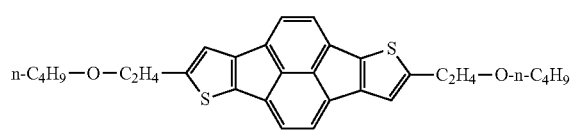
66
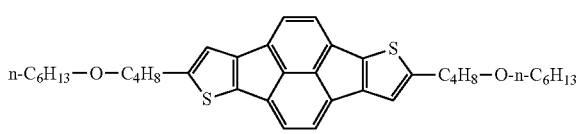

67
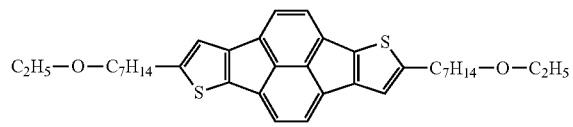
68
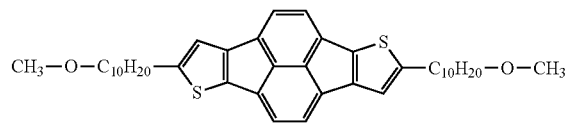
69
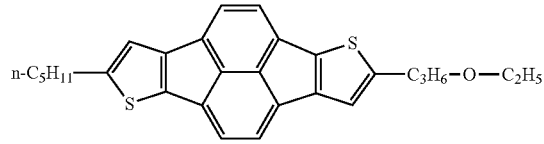
70
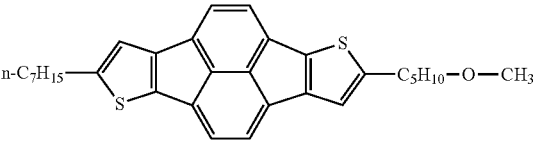
71
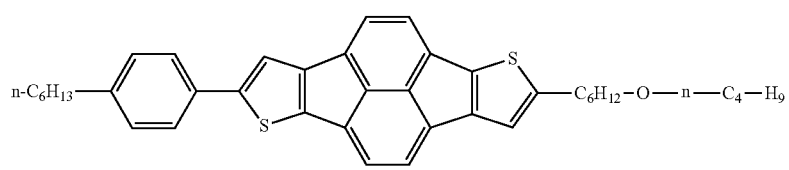
72
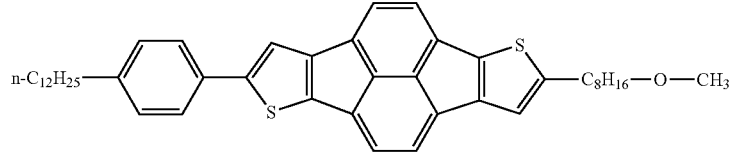
73
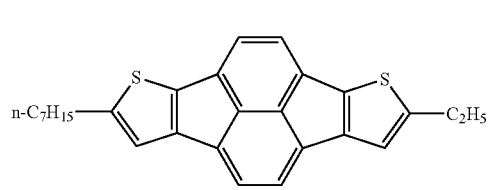
74
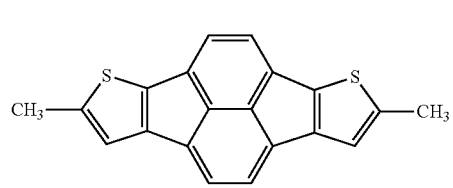
75
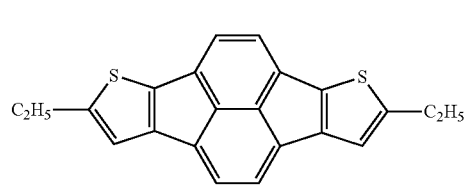
76
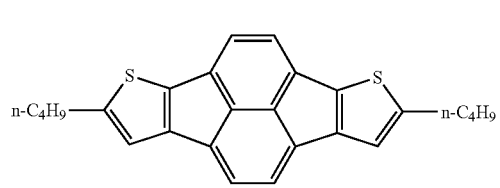
77
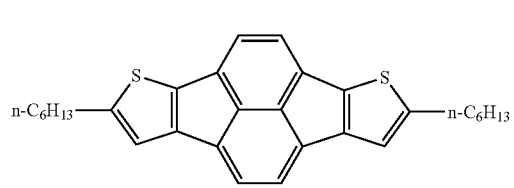
78
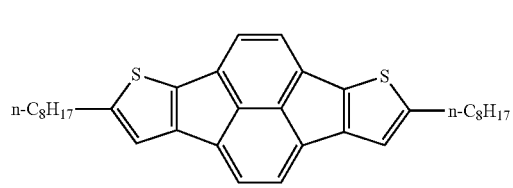
79
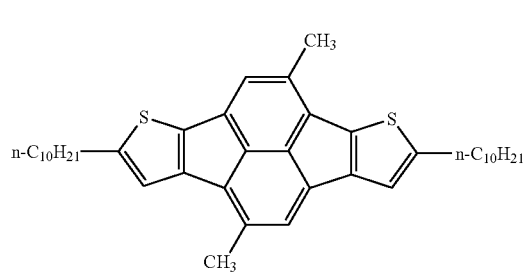
80

-continued
81
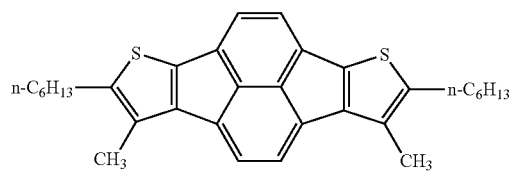
82
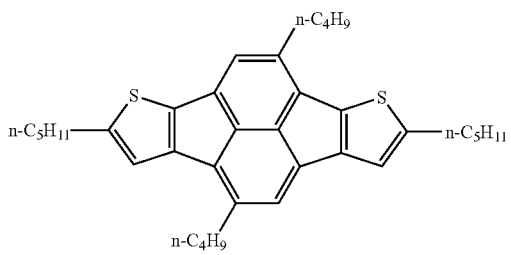
83
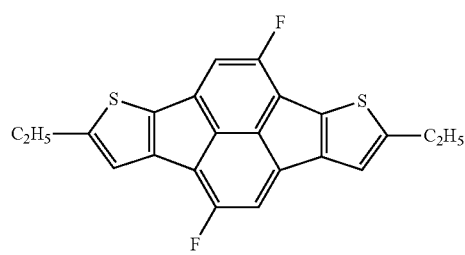
84
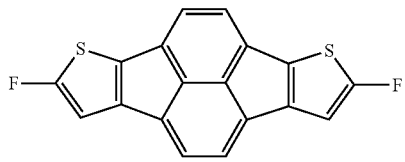
85
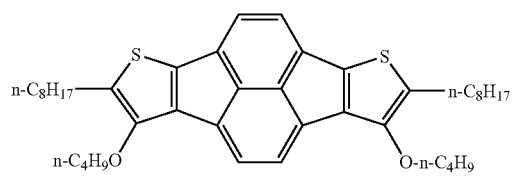
86
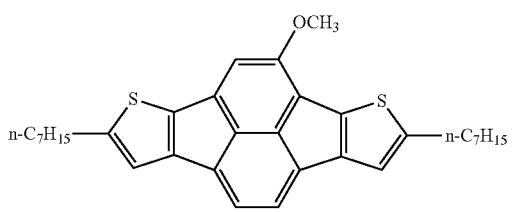
87
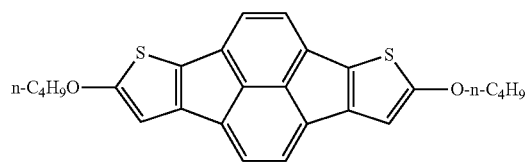
88
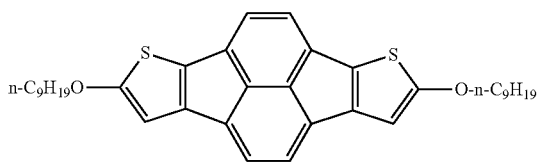
89
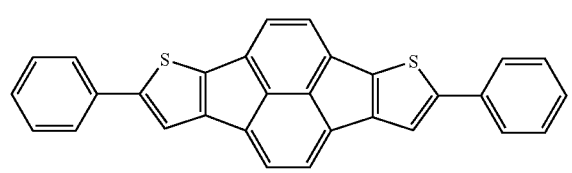
90
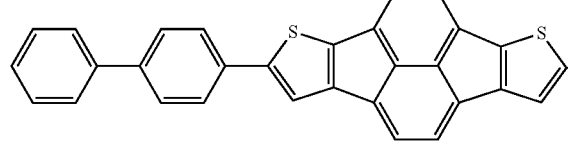
91
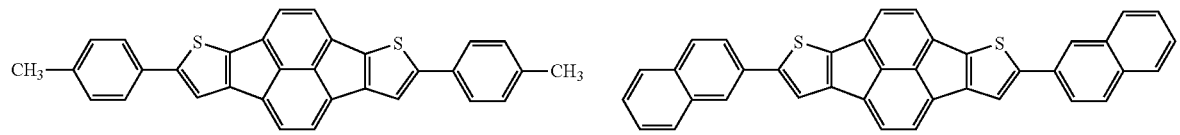
92
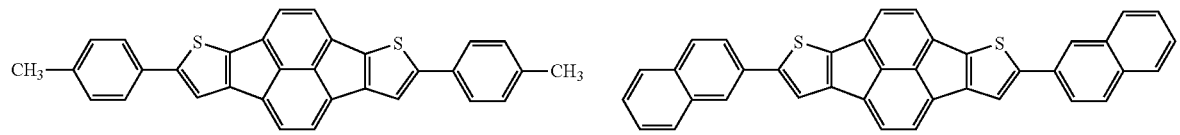
93
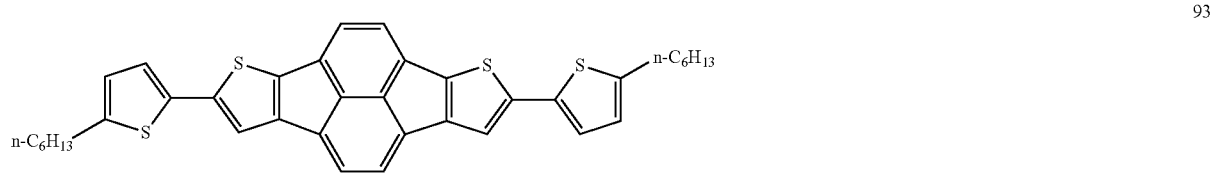

-continued
94
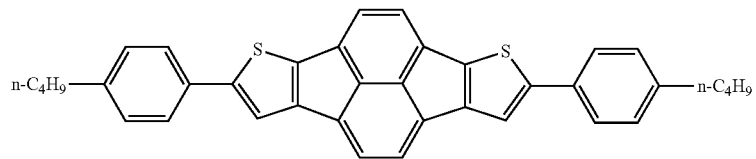
95
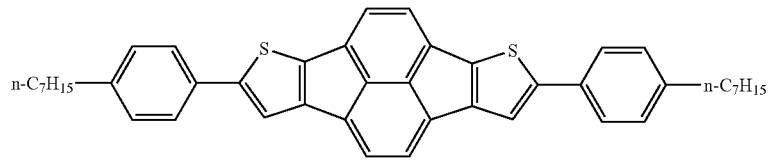
96
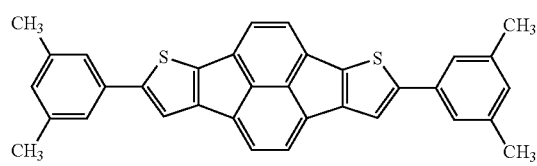
97
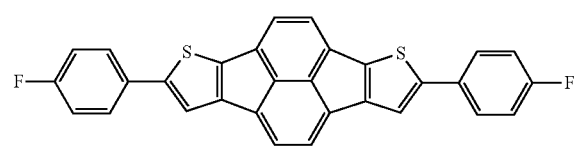
98
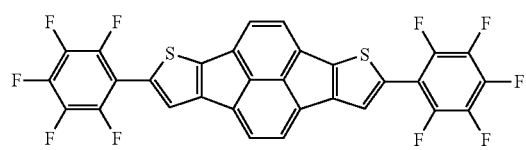
99
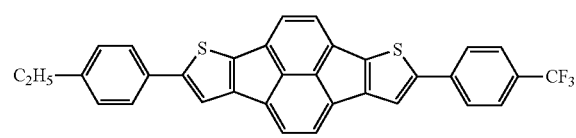
100
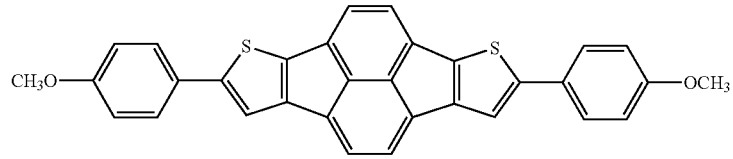
101
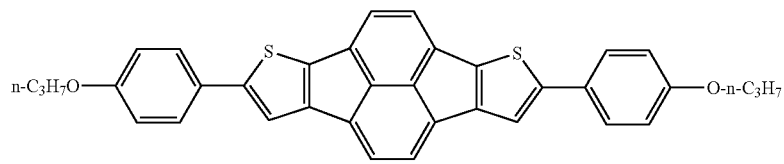
102
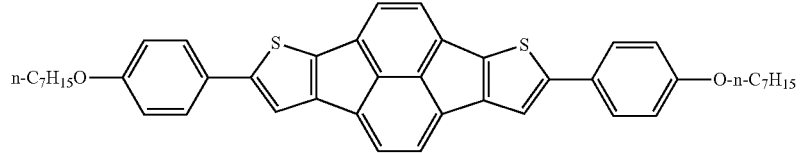
103
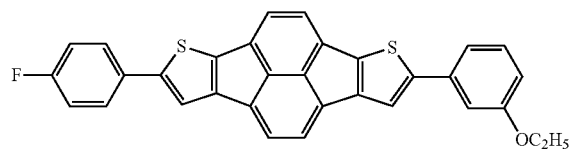
104
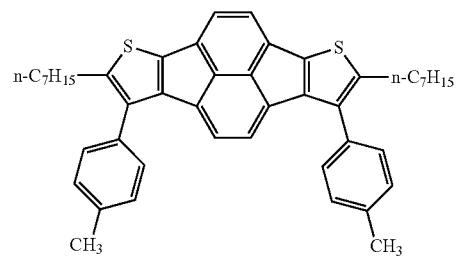

-continued
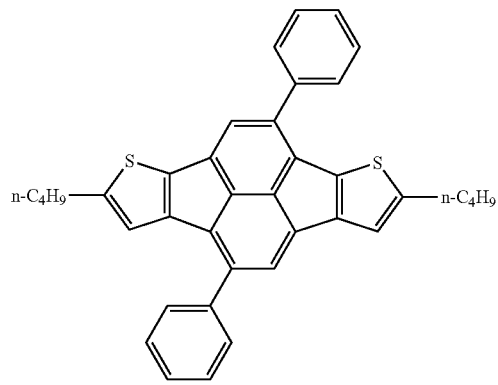
105
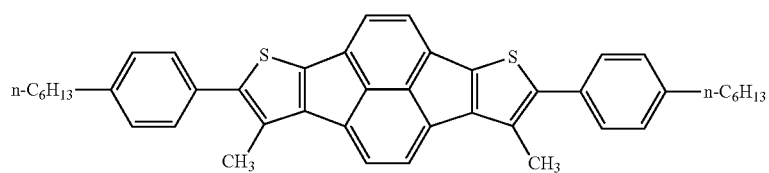
106
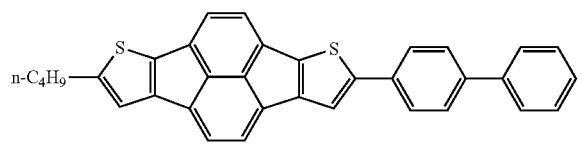
107
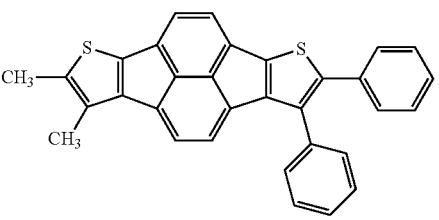
108
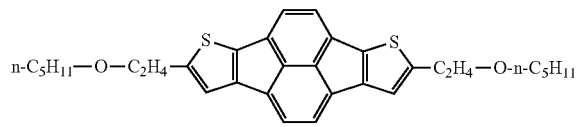
109
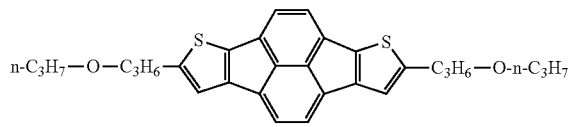
110
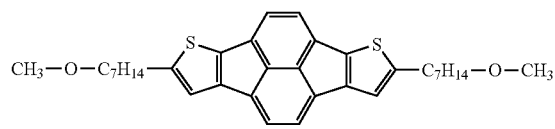
111
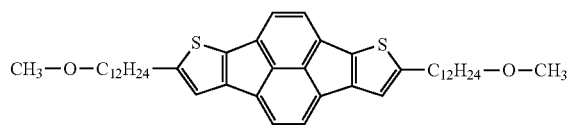
112
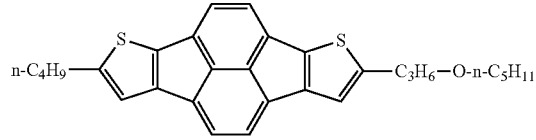
113
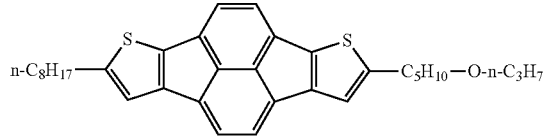
114
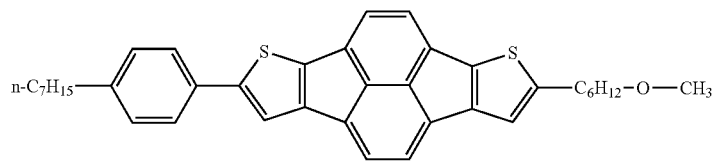
115
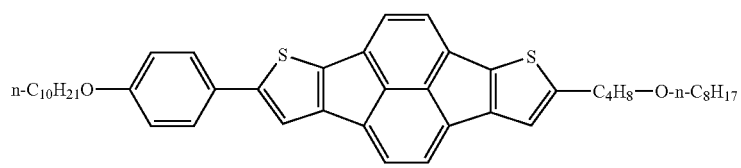
116

-continued
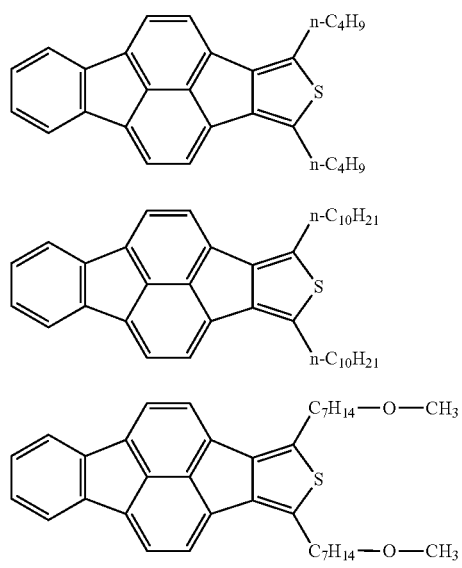
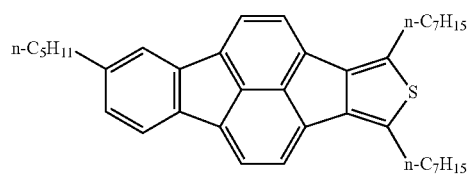
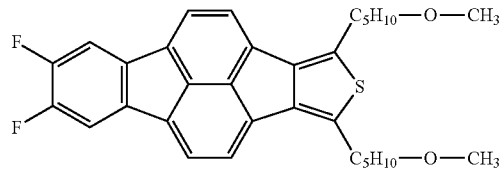
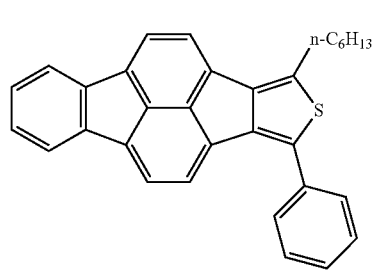
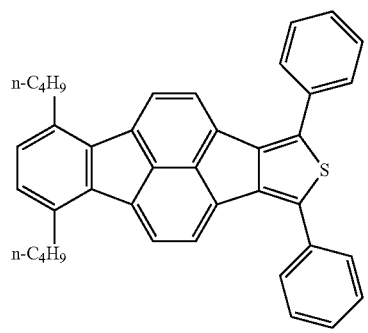
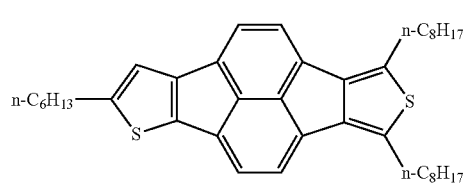
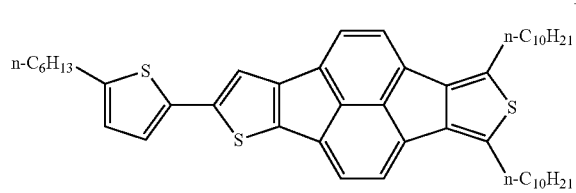
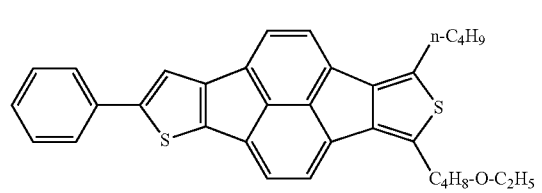
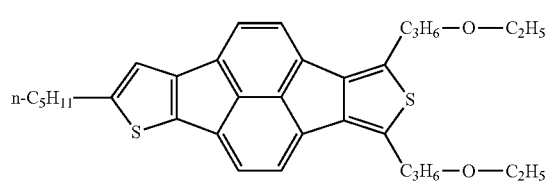
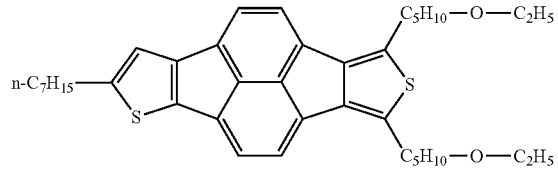

-continued
131
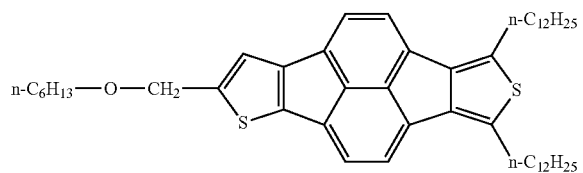
132
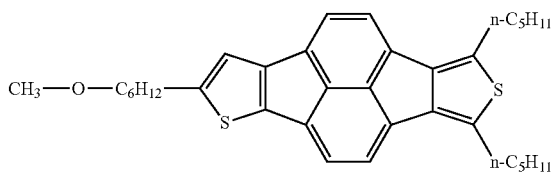
133
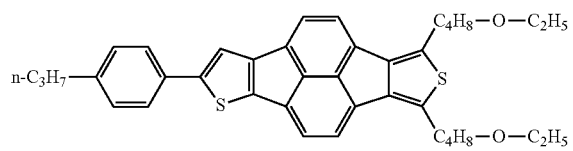
134
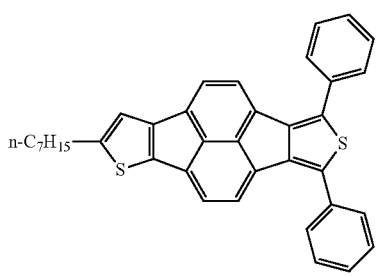
135
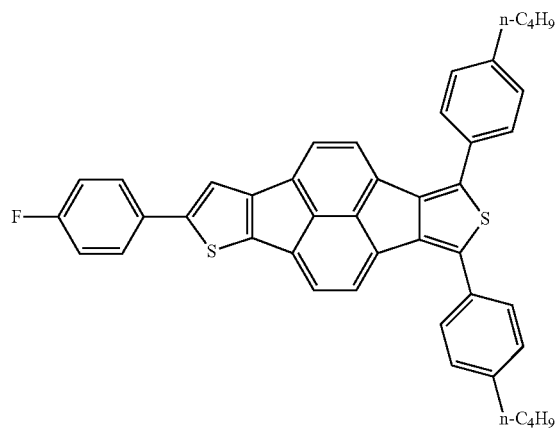
136
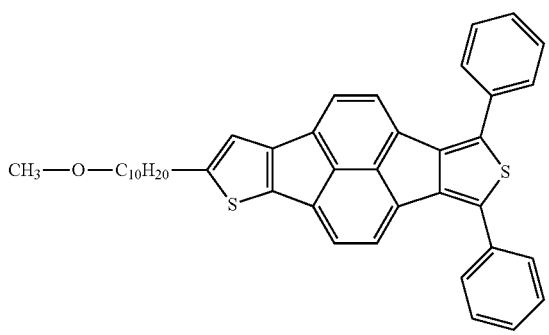
137
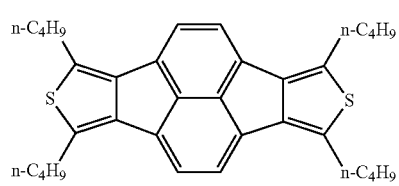
138
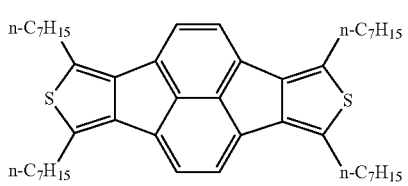
139
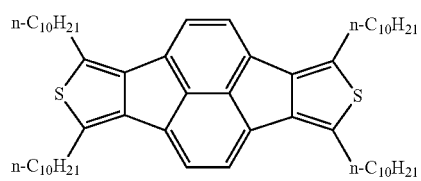
140
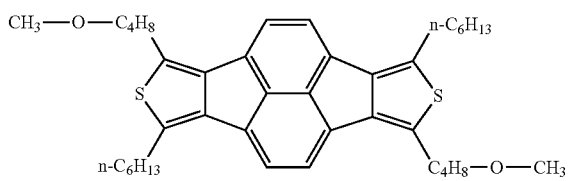
141
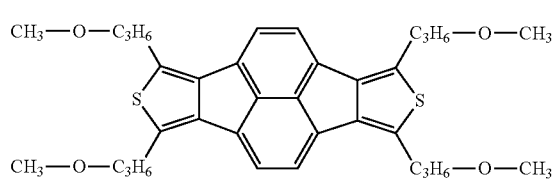
142
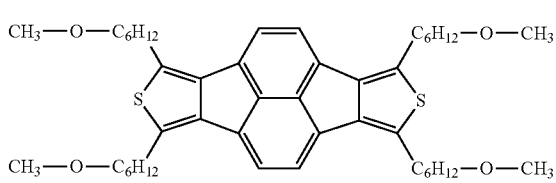

-continued
143 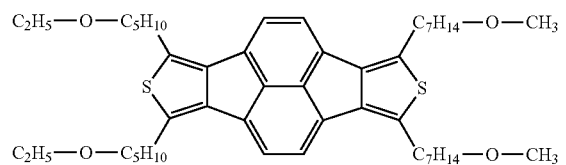
144 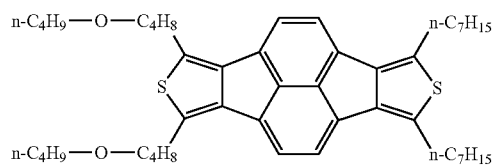
145 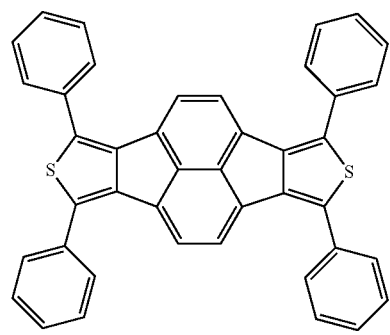
146 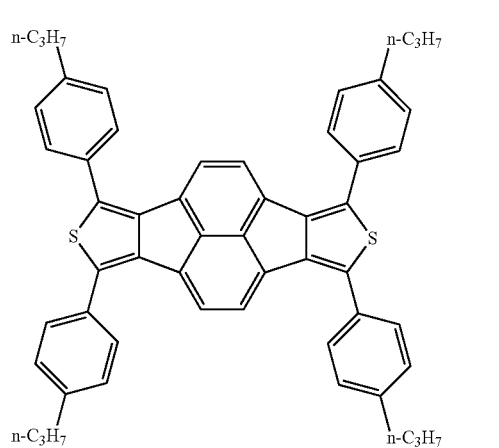
147 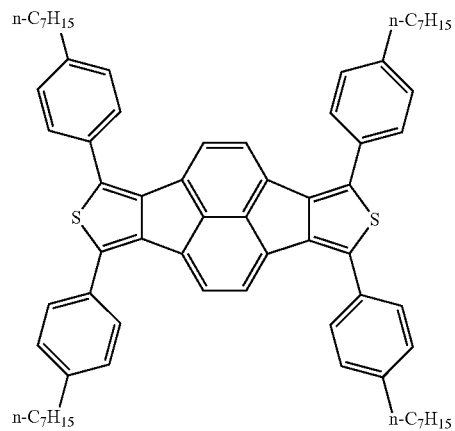
148 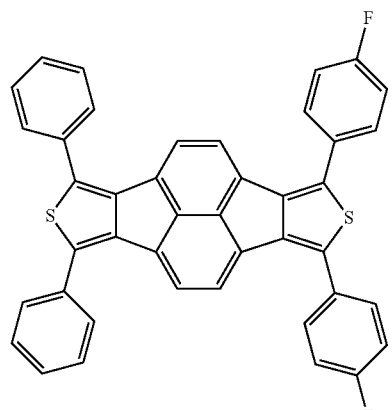
149 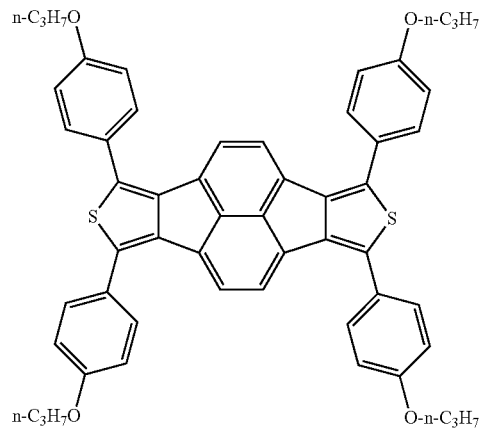
150 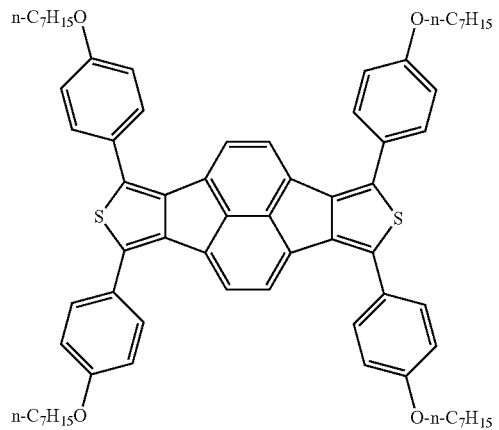

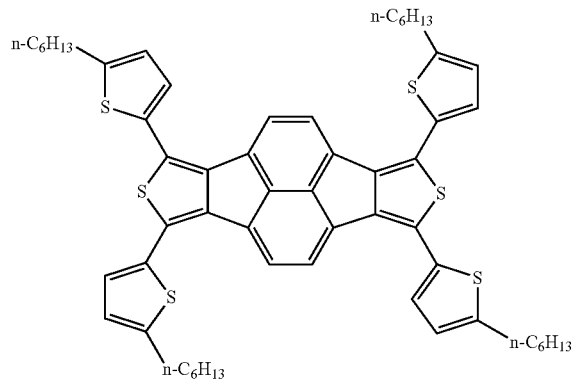

151

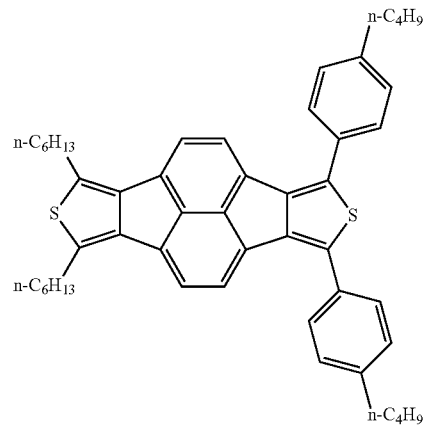

152

With regard to this invention, the compound represented by the general formula (1) can be prepared with reference to methods known in the art.

That is, for example, the compound represented by the general formula (1) can be prepared from the compounds represented by general formula (2) or (3) in the presence of a palladium catalyst (for example, triphenylphosphine palladium chloride, palladium acetate) and a base [see, e.g., the method described in Chem. Rev., 107, 174 (2007)].

Meanwhile, the compound represented by the general formula (2) can be prepared, for example, by reacting the compound represented by the general formula (4) with the compound represented by the general formulas (5) and (6) in the presence of, e.g., a palladium catalyst (for example, triphenylphosphine palladium chloride) and a base [see, e.g., the method described in Chem. Rev., 95, 2457 (1995)].

Meanwhile, the compound represented by the general formula (3) can be prepared, for example, by reacting the compound represented by the general formula (7) with the compound represented by the general formulas (8) and (9) in the presence of, e.g. a palladium catalyst (for example, triphenylphosphine palladium chloride) and a base [see, e.g., the method described in Chem. Rev., 95, 2457 (1995)].

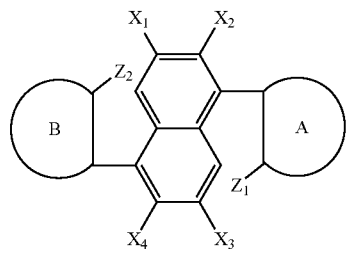

(2)

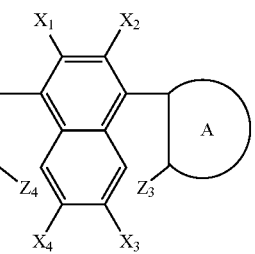

(3)

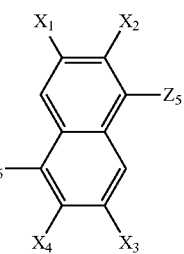

(4)

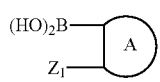

(5)

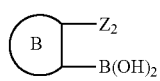

(6)

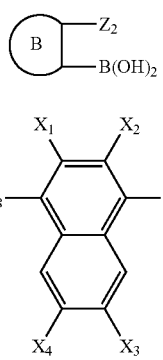

(7)

-continued

[C48]

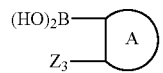

(8)

[C49]

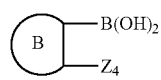

(9)

(wherein $X_1$ to $X_4$, the rings A and B have the same meanings as defined in the general formula (1), and $Z_1$ to $Z_8$ represent a halogen atom)

In the general formulas (2) to (9), the halogen atom represented by $Z_1$ to $Z_8$ is preferably a chlorine atom, a bromine atom, an iodine atom.

Meanwhile, regarding this invention, in some cases, the compound represented by the general formula (1) may be prepared in the form that is in solvation with a solvent used (for example, aromatic hydrocarbon solvents such as toluene and the like). However, such solvates as well as non-solvate forms of the compound represented by the general formula (1) may be used in an organic transistor of this invention. When the compound represented by the general formula (1) is used in an organic transistor, it is preferable to use a high purity compound purified by a purification method such as recrystallization, column chromatography, sublimation purification, or any combination thereof.

An organic transistor has typically a source electrode, a drain electrode and a gate electrode, and a gate-insulating layer, an organic semiconductor layer. For an organic transistor according to this invention, said organic semiconductor layer contains at least one compound represented by the general formula (1).

Embodiments of an organic transistor according to this invention will be now described with reference to the drawings.

FIG. 1 is a schematic cross-sectional view showing one configuration of an organic transistor according to this invention. In this configuration of organic transistor, gate electrode 21 is provided on substrate 11, gate-insulating layer 31 is layered on the gate electrode, source electrode 61 and drain electrode 41 are formed thereon at a predetermined interval, and organic semiconductor layer 51 is further layered thereon (bottom gate•bottom contact structure).

In the configuration of organic transistor shown in FIG. 2, gate electrode 22 is provided on substrate 12, gate insulating layer 32 is layered on the gate electrode, organic semiconductor layer 52 is layered thereon, and source electrode 62 and drain electrode 42 are further formed thereon at a predetermined interval (bottom gate•top contact structure).

Also, in the configuration of organic transistor shown in FIG. 3, source electrode 63 and drain electrode 43 are formed on substrate 13 at a predetermined interval, organic semiconductor layer 53 is layered thereon, gate-insulating layer 33 is layered thereon, and gate electrode 23 is further provided thereon (top gate•bottom contact structure).

In the configuration of organic transistor shown in FIG. 4, organic semiconductor layer 54 is layered on substrate 14, source electrode 64 and drain electrode 44 are formed thereon at a predetermined interval, gate-insulating layer 34 is layered thereon, and gate electrode 24 is further provided thereon (top gate•top contact structure).

In organic transistors having such configurations, the organic semiconductor layer forms a channel area, and an on/off function is worked by controlling the current flow between the source electrode and the drain electrode by a voltage applied in the gate electrode.

A substrate used in an organic transistor of this invention is not particularly limited, but glass, quartz, silicon monocrystal, polycrystal silicon, amorphous silicon, plastic substrate and the like may be generally used. A combined substrate that is formed by combining such materials may be also used, and a single layer structure or a multiple layer structure may be used.

Plastic substrates include, for example, substrates formed from polyethylene terephthalate, polyethylene naphthalate, polyethersulfone, polyetherimide, polyether-etherketone, polyphenylenesulfide, polyarylate, polyimide, polycarbonate, triacetyl-cellulose, cellulose acetate propionate and the like.

Meanwhile, a substrate having conductivity, for example, substrate formed using silicon may be also used as a gate electrode.

In an organic transistor according to this invention, materials used in a source electrode, a drain electrode and a gate electrode are not particularly limited, but any of materials having conductivity may be used.

Materials for the electrodes include, for example, metals or alloys such as indium tin oxide alloy (ITO), tin oxide, gold, silver, platinum, copper, indium, aluminum, magnesium, nickel, chromium, iron, tin, tantalum, palladium, tellurium, iridium, ruthenium, germanium, tungsten, lithium, beryllium, sodium, potassium, calcium, zinc, magnesium/indium alloy, magnesium/copper alloy, magnesium/silver alloy, magnesium/aluminum alloy, chromium/molybdenum alloy, aluminum/lithium alloy, aluminum/scandium/lithium alloy, sodium/potassium alloy and the like, and zinc oxide doped with fluorine, silicon-based materials such as silicon monocrystal, polycrystal silicon, amorphous silicon and the like whose conductivity is increased, carbon materials such as carbon black, graphite, glassy carbon and the like, and indium tin oxide alloy, gold, silver, platinum, copper, indium, aluminum, silicon-based materials with conductivity increased, and carbon materials are more preferably used. These materials may be used as various forms such as a bulk, flakes, particulates and the like.

Also, as materials for the electrodes, conductive polymers whose conductivity is increased by a doping process and the like (for example, polyanilines, polypyrroles, polythiophenes, polyacetylenes, polyparaphenylenes, complexes of polyethylenedioxy-thiophene (PEDOT) and polystyrene-sulfonic acids) are very appropriately used.

Meanwhile, these electrode materials may be used alone or in any combination of two or more materials.

For the source electrode and the drain electrode, among electrode materials listed the above, materials having low impedance at a contact surface with the organic semiconductor layer is preferably used.

A method for forming each electrode is not particularly limited, but it may be formed, for example, from conductive materials by methods such as vapor deposition or sputtering and the like, and may be patterned in a desired shape by a lithography or etching process.

Furthermore, in the case of forming the electrodes using conductive polymers or conductive particulates, they may be formed by patterning a solution or dispersion of conductive polymers, or a dispersion of conductive particulates by an inkjet method, or they may be formed from a coating film by a lithography or a laser abrasion and the like. Also, methods of patterning an ink containing conductive polymers or conductive particulates, a conductive paste (silver paste, carbon paste, etc.) and the like by printing methods such as relief printing, intaglio printing, planographic printing, screen printing and the like may be used.

A film thickness of the source electrode and the drain electrode is not particularly limited, but it is generally set preferably in the range of several nanometers to hundreds micrometers, more preferably 1 nm to 100 µm, even more preferably 10 nm to 20 µm.

Meanwhile, the source electrode and the drain electrode are positioned in faced with each other, and an interval between the source electrode and the drain electrode (channel length) is generally set preferably in the range of hundreds nanometers to several millimeters, more preferably 100 nm to 1 mm, even more preferably 1 µm to 500 µm.

As materials used in a gate-insulating layer, various insulating materials may be used, and inorganic insulators or organic polymer compounds are preferably used.

Inorganic insulators include silicon oxide ($SiO_2$), silicon nitride, aluminum oxide, aluminum nitride, tantalum oxide, titanium oxide, tin oxide, vanadium oxide, barium strontium titanate, barium zirconate titanate, lead zirconate titanate, lead lanthanum titanate, strontium titanate, barium titanate, barium magnesium fluoride, bismuth titanate, strontium bismuth titanate, strontium bismuth tantalate, bismuth tantalate niobate, yttrium trioxide and the like, and silicon oxide, silicon nitride, aluminum oxide, tantalum oxide, titanium oxide is more preferably used.

Methods for forming the gate insulating layer from inorganic insulators include, for example, dry processes such as vacuum vapor deposition, molecular beam epitaxial growth, ion cluster beam, low energy ion beam, ion plating, CVD, sputtering, atmospheric pressure plasma methods and the like, and wet processes such as coating methods such as spray coating, spin coating, blade coating, dip coating, casting, roll coating, bar coating, die coating, air knife, slide hopper, extrusion methods and the like, various printing methods or inkjet methods and the like, and any of these methods may be appropriately selected and applied depending on properties of a material used. In addition, in the case that a silicon-based material is used in the gate electrode, and the gate-insulating layer is formed prior to the formation of an organic semiconductor, the gate-insulating layer may be formed using a thermal oxidation method.

As organic polymer compounds used in the gate insulating layer, polyimides, polyamides, polyesters, polyacrylates, photocurable resins by a photo-radical polymerization, photocurable resins by a photo-cationic polymerization, or copolymers containing acrylonitrile components, polyvinylphenols, polyvinylalcohols, polystyrenes, novolac resins, polyvinylidene fluorides, cyanoethylpullulans and the like may be used. A method for forming the gate-insulating layer from organic polymer compounds is preferably wet processes.

Insulating materials used in the gate-insulating layer may be used alone or in any combination of two or more materials.

Meanwhile, an interface between the gate-insulating layer and the organic semiconductor layer may be treated, for example, with hexamethyldisilazane, octa-decyltrimethoxysilane, octyltrichlorosilane, octadecyltrichlorosilane, benzyltrichloro-silane and the like. Moreover, in the case that an organic polymer compound is used in the gate-insulating layer, and the organic semiconductor layer is formed after the formation of the gate-insulating layer, the gate-insulating layer formed from the organic polymer compound is subject to a rubbing process, and subsequently the organic semiconductor layer may be formed A film thickness of the gate insulating layer is not particularly limited, but it is generally set preferably in the range of several nanometers to several tens micrometers, more preferably 5 nm to 10 µm, even more preferably 10 nm to 5 µm.

An organic transistor according to this invention is formed by containing at least one compound represented by the general formula (1) in an organic semiconductor layer, and the compounds represented by the general formula (1) may be used alone or in any combination of two or more compounds.

Moreover, an organic semiconductor layer may be also formed by using any combination of the compound represented by the general formula (1) with other compounds (for example, polyacetylene derivatives, polythiophene derivatives, poly-thienylene vinylene derivatives, polyphenylene derivatives, polyphenylene vinylene derivatives, polypyrrole derivatives, polyaniline derivatives, polyquinoline derivatives, perylene derivatives, tertracene derivatives, pentacene derivatives, phthalocyanine derivatives, etc.). In this case, a content of the compound represented by the general formula (1) is preferably 20% or more by weight, more preferably 50% or more by weight.

An organic transistor according to this invention acts as a p-type (holes act as carriers), or an n-type (electrons act as carriers) organic transistor, and the p-type organic transistor is preferably used.

A method for forming an organic semiconductor layer is not particularly limited, but methods known in the art may be used.

Methods for forming an organic semiconductor layer include, for example, dry processes such as vacuum vapor deposition, molecular beam epitaxial growth, ion cluster beam, low energy ion beam, ion plating, CVD, sputtering, plasma polymerization methods and the like, and wet processes such as spray coating, spin coating, blade coating, dip coating, casting, roll coating, bar coating, die coating, LB method (Langmuir-Blodgett method), various printing methods, inkjet methods and the like.

In the case of forming an organic semiconductor layer by wet processes, a solution dissolving or dispersing the compound represented by the general formula (1) in an solvent is used.

Solvents include, for example, water, alcohol solvents such as methanol, ethanol, isopropyl alcohol, butanol and the like, ketone solvents such as acetone, methylethyl-ketone, methylisobutylketone, cyclohexanone and the like, ester solvents such as ethyl acetate, butyl acetate and the like, ether solvents such as diethylether, dioxane, tetra-hydrofuran, anisole and the like, hydrocarbon solvents such as hexane, octane, toluene, xylene, ethylbenzene, cumene and the like, halogenated hydrocarbon solvents such as dichloromethane, chloroform, dichloroethan, tetrachloroethan, tetrachloroethylene, chlorobenzene, fluorobenzene, dichlorobenzene, trichlorobenzene and the like, nitrile solvents such as acetonitrile, propionitrile, methoxyacetonitrile, glutardinitrile, benzo-nitrile and the like, aprotic polar solvents such as dimethylsulfoxide, sulfolane, N,N-dimethylformamide, N,N-dimethylacetamide, N-methyl-2-pyrrolidone and the like. Such solvents may be used alone or in any combination of two or more solvents.

A film thickness of an organic semiconductor layer is not particularly limited, but it is generally set preferably in the range of several nanometers to several tens micrometers, more preferably 1 nm to 10 µm, even more preferably 5 nm to 1 µm.

In an organic transistor according to this invention, the organic semiconductor layer may be subject to a doping process as desired.

Meanwhile, as a dopant, both donor-type and acceptor-type dopants may be used, and the acceptor-type dopant is preferably used.

As donor-type dopants, any of compounds having the functionality providing electrons for organic compounds in an organic semiconductor layer may be very suitably used.

Donor-type dopants include, for example, alkali metals such as Li, Na, K, Rb, Cs and the like, alkaline earth metals such as Ca, Sr, Ba and the like, rare earth metals such as Y, La, Ce, Pr, Nd, Sm, Eu, Gd, Tb, Dy, Ho, Er, Yb and the like, ammonium ion, $R_4P^+$ (R represents an alkyl group), $R_4As^+$ (R represents an alkyl group), $R_3S^+$ (R represents an alkyl group), acetylcholine and the like.

As acceptor-type dopants, any of compounds having the functionality removing electrons from organic compounds in an organic semiconductor layer may be very suitably used.

Acceptor-type dopants include, for example, halogen compounds such as $Cl_2$, $Br_2$, $I_2$, ICl, $ICl_3$, IBr, IF and the like, Lewis acids such as $PF_5$, $AsF_6$, $SbF_5$, $BF_3$, $BCl_3$, $BBr_3$, $SO_3$ and the like, protic acids such as HF, HCl, $HNO_3$, $H_2SO_4$, $HClO_4$, $FSO_3H$, $ClSO_3H$, $CF_3SO_3H$ and the like, organic acids such as acetic acid, formic acid, amino acid and the like, transition metal compounds such as $FeCl_3$, FeOCl, $TiCl_4$, $ZrCl_4$, $HfCl_4$, $NbF_5$, $NbCl_5$, $TaCl_6$, $MoCl_6$, $WF_5$, $WCl_6$, $UF_6$, $LnCl_3$ (Ln=lanthanoids such as La, Ce, Nd, Pr and the like and Y) and the like, electrolytic anions such as $Cl^-$, $Br^-$, $I^-$, $ClO_4^-$, $PF_6^-$, $AsF_5^-$, $SbF_6^-$, $BF_4^-$, sulfonic acid anion and the like.

Meanwhile, as doping methods, methods in which a dopant is introduced during or after the formation of an organic semiconductor layer may be used.

Moreover, in order to reduce an effect of oxygen or moisture in air, an organic transistor according to this invention may be also provided for a gas barrier layer in all or part of the circumference side of an organic transistor. Materials that can form the gas barrier layer include, for example, polyvinyl alcohols, ethylene-vinyl alcohol copolymers, polyvinyl chlorides, polyvinylidene chlorides and the like. In addition, inorganic insulators listed as materials used in the gate-insulating layer may be also used in the formation of the gas barrier layer.

Meanwhile, an organic transistor according to this invention may be used in, e.g., liquid crystal display devices, organic electroluminescence devices, electronic papers, various sensors, RFIDs (radio frequency identification cards) and the like.

EXAMPLES

In the following, this invention will be described in more detail by the examples, but this invention should not be limited to these examples.

Example 1

A thermal oxidation film ($SiO_2$) in a thickness of 200 nm was formed on a silicon substrate having an impedance of 0.02 Ω·cm as a gate electrode. Herein, the silicon substrate itself becomes the gate electrode and $SiO_2$ layer formed on the surface of the silicon substrate becomes a gate-insulating layer. An organic semiconductor layer was formed on the gate-insulating layer by vapor depositing the compound of Exemplary compound No. 2 in a thickness of 30 nm at a deposition rate of 0.03 nm/sec under vacuum ($5\times10^{-4}$ Pa). Moreover, a source electrode and a drain electrode were formed on the organic semiconductor layer by vapor depositing gold using a mask. Meanwhile, a thickness of the source electrode and the drain electrode was respectively 40 nm, a channel width was 5 mm, and a channel length was 20 μm.

The organic transistor thus manufactured showed the properties of a p-type transistor element. The charge mobility was calculated from the saturated area of the current-voltage (I-V) property of this organic transistor.

Moreover, a drain current value when a drain bias was −50 V and a gate bias was −50 V and 0 V was measured, and the current on/off ratio was calculated.

Furthermore, the charge mobility and current on/off ratio were measured again after storing the manufactured organic transistor element in air at 25° C. for one month. The results were shown in Table 1.

Examples 2 to 20

Organic transistors were manufactured by the method described in Example 1, except for using the compounds of Exemplary compound No. 5 (Example 2), Exemplary compound No. 10 (Example 3), Exemplary compound No. 17 (Example 4), Exemplary compound No. 20 (Example 5), Exemplary compound No. 32 (Example 6), Exemplary compound No. 34 (Example 7), Exemplary compound No. 45 (Example 8), Exemplary compound No. 48 (Example 9), Exemplary compound No. 50 (Example 10), Exemplary compound No. 54 (Example 11), Exemplary compound No. 65 (Example 12), Exemplary compound No. 78 (Example 13), Exemplary compound No. 92 (Example 14), Exemplary compound No. 101 (Example 15), Exemplary compound No. 110 (Example 16), Exemplary compound No. 117 (Example 17), Exemplary compound No. 125 (Example 18), Exemplary compound No. 137 (Example 19), Exemplary compound No. 145 (Example 20), respectively, instead of using the compound of Exemplary compound No. 2 in the formation of the organic semiconductor layer in Example 1.

Moreover, the properties of these organic transistors were investigated by the methods described in Example 1, and the results were shown in Table 1.

Comparative Example 1

The organic transistor was manufactured by the method described in Example 1, except for using pentacene instead of using the compound of Exemplary compound No. 2 in the formation of the organic semiconductor layer in Example 1.

Moreover, the properties of this organic transistor were investigated by methods as in Example 1, and the results were shown in Table 1. Meanwhile, after leaving for one month, it did not show the properties of the organic transistor.

Comparative Example 2

The organic transistor was manufactured by the method described in Example 1, except for using α-hexathienylene instead of using the compound of Exemplary compound No. 2 in the formation of the organic semiconductor layer in Example 1.

Moreover, the properties of this organic transistor were investigated by methods as in Example 1, and the results were shown in Table 1.

Comparative Example 3

The organic transistor was manufactured by the method described in Example 1, except for using dibenzo[a,j]naphthacene instead of using the compound of Exemplary compound No. 2 in the formation of the organic semiconductor layer in Example 1.

Moreover, the properties of this organic transistor were investigated by methods as in Example 1, and the results were shown in Table 1.

Comparative Example 4

The organic transistor was manufactured by the method described in Example 1, except for using dibenzo[de,qr]naphthacene instead of using the compound of Exemplary compound No. 2 in the formation of the organic semiconductor layer in Example 1.

Moreover, the properties of this organic transistor were investigated by methods as in Example 1, and the results were shown in Table 1.

Example 21

A thermal oxidation film ($SiO_2$) in a thickness of 200 nm was formed on a silicon substrate having an impedance of 0.02 Ω·cm as a gate electrode. Herein, the silicon substrate itself becomes the gate electrode and $SiO_2$ layer formed on the surface of the silicon substrate becomes a gate-insulating layer. A solution of the compound of Exemplary compound No. 35 in chlorobenzene (concentration: 0.3% by weight) was coated on the silicon substrate that was heated to 80° C., thereby forming an organic semiconductor layer which comprises the compound of Exemplary compound No. 35 in a thickness of 50 nm by the evaporation of chlorobenzene. Moreover, a source electrode and a drain electrode were formed on the organic semiconductor layer by vapor depositing gold using a mask. Meanwhile, a thickness of the source electrode and the drain electrode was respectively 40 nm, a channel width was 5 mm, and a channel length was 20 μm. Furthermore, the properties of this organic transistor were investigated by the methods described in Example 1, and the mobility was $4.1 \times 10^{-2}$ ($cm^2$/Vsec) and the current on/off ratio was $3.0 \times 10^5$.

Example 22

The organic transistor was manufactured by the method described in Example 21, except for using the compound of Exemplary compound No. 67 instead of using the compound of Exemplary compound No. 35 in the formation of the organic semiconductor layer in Example 21.

Moreover, the properties of this organic transistor were investigated by methods as in Example 1, and the mobility was $3.0 \times 10^{-2}$ ($cm^2$/Vsec) and the current on/off ratio was $3.6 \times 10^5$.

Example 23

The organic transistor was manufactured by the method described in Example 21, except for using the compound of Exemplary compound No. 79 instead of using the compound of Exemplary compound No. 35 in the formation of the organic semiconductor layer in Example 21.

Moreover, the properties of this organic transistor were investigated by methods as in Example 1, and the mobility was $3.9 \times 10^{-2}$ ($cm^2$/Vsec) and the current on/off ratio was $2.7 \times 10^5$.

Example 24

The organic transistor was manufactured by the method described in Example 21, except for using the compound of Exemplary compound No. 138 instead of using the compound of Exemplary compound No. 35 in the formation of the organic semiconductor layer in Example 21.

Moreover, the properties of this organic transistor were investigated by methods as in the example 1, and the mobility was $2.8 \times 10^{-2}$ ($cm^2$/Vsec) and the current on/off ratio was $3.5 \times 10^5$.

TABLE 1

| Organic transistor | Immediately after manufacturing | | After leaving for 1 month | |
|---|---|---|---|---|
| | Mobility ($cm^2$/Vsec) | On/off ratio | Mobility ($cm^2$/Vsec) | On/off ratio |
| Example 1 | $5.5 \times 10^{-2}$ | $3.2 \times 10^5$ | $5.4 \times 10^{-2}$ | $3.1 \times 10^5$ |
| Example 2 | $6.0 \times 10^{-2}$ | $3.7 \times 10^5$ | $5.8 \times 10^{-2}$ | $3.6 \times 10^5$ |
| Example 3 | $5.4 \times 10^{-2}$ | $3.5 \times 10^5$ | $5.3 \times 10^{-2}$ | $3.3 \times 10^5$ |
| Example 4 | $6.8 \times 10^{-2}$ | $3.0 \times 10^5$ | $6.6 \times 10^{-2}$ | $2.8 \times 10^5$ |
| Example 5 | $5.2 \times 10^{-2}$ | $3.4 \times 10^5$ | $4.9 \times 10^{-2}$ | $3.3 \times 10^5$ |
| Example 6 | $5.4 \times 10^{-2}$ | $2.9 \times 10^5$ | $5.2 \times 10^{-2}$ | $2.8 \times 10^5$ |
| Example 7 | $5.8 \times 10^{-2}$ | $3.3 \times 10^5$ | $5.6 \times 10^{-2}$ | $3.1 \times 10^5$ |
| Example 8 | $4.7 \times 10^{-2}$ | $3.1 \times 10^5$ | $4.6 \times 10^{-2}$ | $3.0 \times 10^5$ |
| Example 9 | $5.7 \times 10^{-2}$ | $2.9 \times 10^5$ | $5.5 \times 10^{-2}$ | $2.8 \times 10^5$ |
| Example 10 | $7.1 \times 10^{-2}$ | $3.5 \times 10^5$ | $7.0 \times 10^{-2}$ | $3.4 \times 10^5$ |
| Example 11 | $5.8 \times 10^{-2}$ | $3.3 \times 10^5$ | $5.6 \times 10^{-2}$ | $3.2 \times 10^5$ |
| Example 12 | $5.5 \times 10^{-2}$ | $3.5 \times 10^5$ | $5.4 \times 10^{-2}$ | $3.4 \times 10^5$ |
| Example 13 | $4.6 \times 10^{-2}$ | $3.2 \times 10^5$ | $4.5 \times 10^{-2}$ | $3.1 \times 10^5$ |
| Example 14 | $5.4 \times 10^{-2}$ | $3.6 \times 10^5$ | $5.3 \times 10^{-2}$ | $3.4 \times 10^5$ |
| Example 15 | $5.6 \times 10^{-2}$ | $2.9 \times 10^5$ | $5.5 \times 10^{-2}$ | $2.8 \times 10^5$ |
| Example 16 | $4.5 \times 10^{-2}$ | $3.2 \times 10^5$ | $4.4 \times 10^{-2}$ | $3.1 \times 10^5$ |
| Example 17 | $3.0 \times 10^{-2}$ | $3.5 \times 10^5$ | $2.8 \times 10^{-2}$ | $3.4 \times 10^5$ |
| Example 18 | $3.2 \times 10^{-2}$ | $3.1 \times 10^5$ | $3.1 \times 10^{-2}$ | $2.9 \times 10^5$ |
| Example 19 | $3.8 \times 10^{-2}$ | $3.5 \times 10^5$ | $3.6 \times 10^{-2}$ | $3.3 \times 10^5$ |
| Example 20 | $3.2 \times 10^{-2}$ | $3.4 \times 10^5$ | $3.0 \times 10^{-2}$ | $3.3 \times 10^5$ |
| Com. Ex. 1 | $3.2 \times 10^{-5}$ | $2.2 \times 10^1$ | Undetectable | Undetectable |
| Com. Ex. 2 | $1.0 \times 10^{-2}$ | $1.2 \times 10^3$ | $2.0 \times 10^{-4}$ | $1.1 \times 10^1$ |
| Com. Ex. 3 | $2.8 \times 10^{-5}$ | $2.1 \times 10^5$ | $2.2 \times 10^{-5}$ | $1.9 \times 10^5$ |
| Com. Ex. 4 | $2.1 \times 10^{-5}$ | $1.8 \times 10^5$ | $1.7 \times 10^{-5}$ | $1.4 \times 10^5$ |

From the Table 1, it is clear that an organic transistor according to this invention is the excellent organic transistor having good properties such as high charge mobility, a high current on/off ratio, simultaneously with excellent stability in that changes in the organic transistor over time are inhibited.

INDUSTRIAL APPLICABILITY

Since an organic transistor according to this invention has high charge mobility, a high current on/off ratio, and excellent storage stability, it can be used in liquid crystal display devices, organic electroluminescent devices, electronic papers, various sensors, RFIDs (radio frequency identification cards) and the like.

The invention claimed is:

1. An organic transistor comprising an organic semiconductor layer wherein said organic semiconductor layer comprises at least one compound represented by the general formula (1):

[C1]

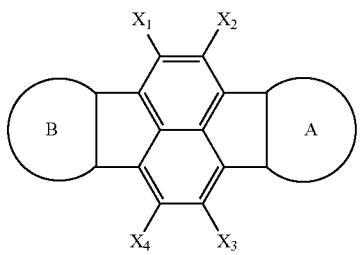

(1)

(wherein each of $X_1$ to $X_4$ represents independently a hydrogen atom, a halogen atom, a straight, branched or cyclic alkyl group, a straight, branched or cyclic alkoxy group, a straight, branched or cyclic alkoxyalkyl group, or an unsubstituted or substituted aryl group, A represents an unsubstituted or substituted thiophene ring, B represents an unsubstituted or substituted benzene ring, or an unsubstituted or substituted thiophene ring).

2. The organic transistor according to claim 1, wherein said compound represented by the general formula (1) is a compound represented by the general formula (1-A) or (1-B):

[C2]

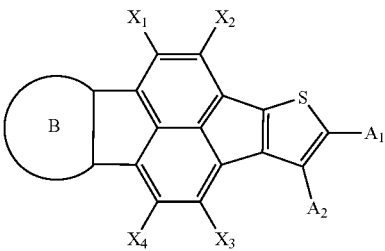

(1-A)

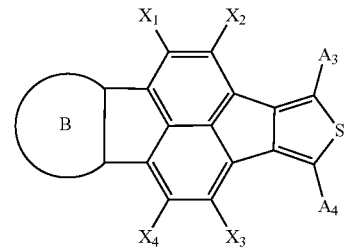

(1-B)

(wherein $X_1$ to $X_4$ and the ring B have the same meanings as defined in the general formula (1), each of $A_1$ to $A_4$ represents independently a hydrogen atom, a halogen atom, a straight, branched or cyclic alkyl group, a straight, branched or cyclic alkoxy group, a straight, branched or cyclic alkoxyalkyl group, or an unsubstituted or substituted aryl group).

* * * * *